US007842835B2

(12) United States Patent
Kozikowski et al.

(10) Patent No.: US 7,842,835 B2
(45) Date of Patent: Nov. 30, 2010

(54) HISTONE DEACETYLASE INHIBITORS AND METHODS OF USE THEREOF

(75) Inventors: Alan P. Kozikowski, Arlington, VA (US); Anatoly Dritschilo, Bethesda, MD (US); Mira Jung, Rockville, MD (US); Pavel A. Petukhov, Rockville, MD (US); Bin Chen, Arlington, VA (US)

(73) Assignee: Georgetown University, Washington, DC (US)

( * ) Notice: Subject to any disclaimer, the term of this patent is extended or adjusted under 35 U.S.C. 154(b) by 37 days.

(21) Appl. No.: 10/614,498

(22) Filed: Jul. 7, 2003

(65) Prior Publication Data

US 2005/0014839 A1    Jan. 20, 2005

(51) Int. Cl.
C07C 275/04 (2006.01)
A61K 31/17 (2006.01)
(52) U.S. Cl. .................. 564/32; 564/48; 514/588; 514/595
(58) Field of Classification Search .................. 564/32, 564/48; 514/588, 595
See application file for complete search history.

(56) References Cited

U.S. PATENT DOCUMENTS

| 4,028,401 | A  | 6/1977  | Fessler et al.    |
| 4,122,186 | A  | 10/1978 | Lafon             |
| 5,700,811 | A  | 12/1997 | Breslow et al.    |
| 5,776,494 | A  | 7/1998  | Guskey et al.     |
| 6,495,719 | B2 | 12/2002 | Lan-Hargest et al.|
| 6,511,990 | B1 | 1/2003  | Breslow et al.    |
| 2002/0103192 | A1 | 8/2002  | Curtin et al.     |
| 2002/0115826 | A1 | 8/2002  | Delorme et al.    |
| 2002/0143037 | A1 | 10/2002 | Lan-Hargest et al.|
| 2002/0143052 | A1 | 10/2002 | Lan-Hargest et al.|
| 2002/0143196 | A1 | 10/2002 | Lan-Hargest et al.|
| 2005/0119305 | A1 | 6/2005  | Naka et al.       |

FOREIGN PATENT DOCUMENTS

| WO | WO 93/07148   |         | 4/1993  |
| WO | WO-95/31977   |         | 11/1995 |
| WO | WO 98/18754   |         | 5/1998  |
| WO | WO 01/38322   | A1      | 5/2001  |
| WO | WO 01/70675   | A2      | 9/2001  |
| WO | WO 01/70734   | A2      | 9/2001  |
| WO | WO 02/26696   | A1      | 4/2002  |
| WO | WO-02/074298  |         | 9/2002  |
| WO | WO 02/076941  | A2      | 10/2002 |

OTHER PUBLICATIONS

Victoria Richon et al A class of hybrid polar inducers of transformed cell differentiation inhibits histone deacetylase, 1998.*
Design of Nove Histone deacetylase inhibitors, Phieng Siliphaivanh et al, 2007.*

Exploration of internal cavity of histone deacetylase (HDAC) with selective HDAC1/HDAC2 inhibitors (SHI-1:2). Methot Joey et al, 2008.*
Ommeslaeghe, et al., "Amide analogues of TSA: synthesis, binding mode analysis and HDAC inhibition." *Bioorg Med Chem Lett*. Jun. 2, 2003;13(11):1861-4.
Meyn, MS, "Ataxia-telangiectasia and cellular responses to DNA damage." *J. Am Assoc. for Cancer Res*. Dec. 15, 1995;55(24):5991-6001. Review.
Jackson et al., "DNA double-strand break repair and V(D)J recombination: involvement of DNA-PK." *Elsevier Sc. Ltd*. Oct. 1995;20(10):412-415. Review.
Björklund et al., "Global transcription regulators of eukaryotes." *Cell*. Mar. 19, 1999;96(6):759-67.
Zhang et al., "HDAC-6 interacts with and deacetylates tubulin and microtubules in vivo." *EMBO J*. Mar. 3, 2003;22(5):1168-79.
Weichselbaum et al., "Heterogeneity of radiation response of a parent human epidermoid carcinoma cell line and four clones." *Int J Radial Oncol Biol Phys*. May 1988;14(5):907-12.
Dai et al., "Indole amide hydroxamic acids as potent inhibitors of histone deacetylases." *Bioorg Med Chem Lett*. Jun. 2, 2003;13(11):1897-901.
Oleinick et al., "Nuclear structure and the microdistribution of radiation damage in DNA." *Int. J. Radiat. Biol*. 1994;66(5):523-529.
Stockdale FE. 1978. "Ch IV: Principle of cancer patient management",*In 12: Oncology, In Scientific American Medicine*, vol. 3. NY:Scientific American, Inc.:1-10.
Struhl et al., "The TAFs in the HAT." *Cell*. Jul. 10, 1998;94(1):1-4. Review.
Kornberg et al., "Twenty-five years of the nucleosome, fundamental particle of the eukaryote chromosome." *Cell*. Aug. 6, 1999;98(3):285-94. Review.
Hilger et al., "Tc(V) and Re(V) complexes of N- (mercaptoacetylglycyl) -histamine," Database accession No. 1998:190659, Abstract, XP-002430349.
Katsarava et al., "Role of complex formation during polycondensation of activated N-hydroxysuccinimide esters with diamines," Database accession No. 1984:531205, Abstract, XP-002430347.
Kornyei et al., "99mTc-labeling of mercaptoacetyltriglycine and its related compounds," Database accession No. 1994:186299, Abstract, XP-002430351.
Noll et al, "Note on the fast hydrolsis of the methyl ester of mercaptoacetyl diglycine during complexation with Tc/Re(v) gluconate," Database accession No. 1997:321173, Abstract, XP-002430350.
Ranadive et al., "Reactions of amines with N-hydroxy-, (2,3-epoxypropoxy) succinimide and—naptthalimide," Database accession No. 1995:333422, Abstract, XP-002430348.
Ranadive & Samant, "Reactions of amines with N-hydroxy-, N-(2,3-epoxypropoxy)-succinimide and naphthalimide," Indian Journal of Chemistry 34B:102-106 (1995).

(Continued)

*Primary Examiner*—Rita J Desai
(74) *Attorney, Agent, or Firm*—Foley Hoag, LLP

(57) ABSTRACT

The invention provides novel classes of HDAC inhibitors. Methods of sensitizing a cancer cell to the cytotoxic effects of radiotherapy are also provided as well as methods for treating cancer and methods for treating neurological diseases. Additionally, the invention further provides pharmaceutical compositions comprising an HDAC inhibitor of the invention, and kits comprising a container containing an HDAC inhibitor of the invention.

11 Claims, 1 Drawing Sheet

OTHER PUBLICATIONS

Figure 1:
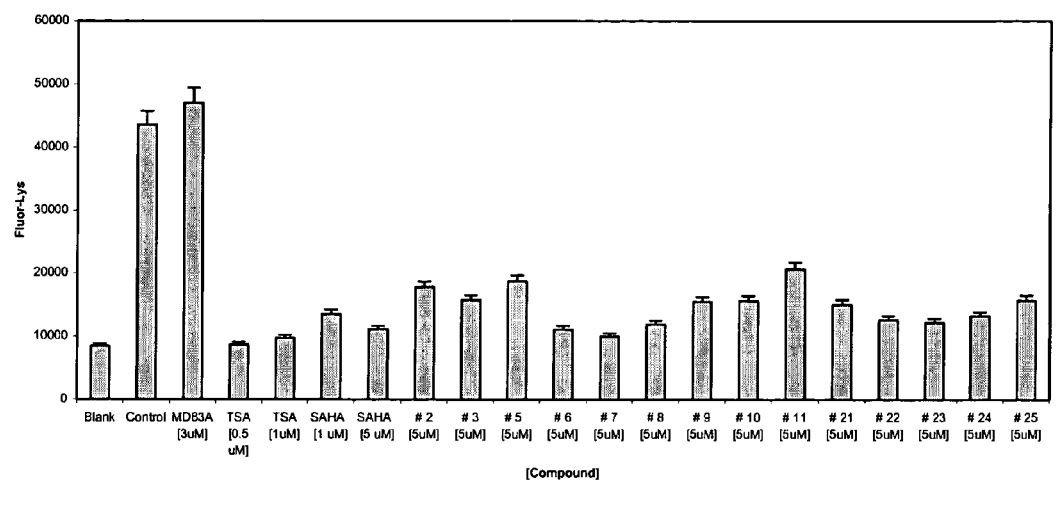

Sternson et al., "Synthesis of 7200 Small Molecules Based on a Substructural Analysis of the Histone Deacetylase Inhibitors Trichostatin and Trapoxin," Organic Letters 3(26):4239-4242 (2001).

Caplus English Abstract, DN 48:11270 GB 679323 Aktiebolaget Pharmacia.

Martirosyan et al., "Differentiation-inducing quinolines as experimental breast cancer agents in the MCF-7 human breast cancer cell model," Biochemical Pharmacology, 68:1729-1738 (2004).

* cited by examiner

HISTONE DEACETYLASE INHIBITORS AND METHODS OF USE THEREOF

1. FIELD OF THE INVENTION

The present invention relates to histone deacetylase ("HDAC") inhibitors, pharmaceutical compositions comprising an HDAC inhibitor, methods of increasing the sensitivity of a cancer cell to the cytotoxic effects of radiotherapy comprising contacting said cell with an HDAC inhibitor, and methods of treating cancer or a neurological disease comprising administering to a subject in need thereof, an HDAC inhibitor.

2. BACKGROUND OF THE INVENTION

2.1 Cancer

Cancer is the second leading cause of death in the United States after heart disease. The American Cancer Society estimated that in 2002, there were 1.3 million new cases of cancer and 555,000 cancer-related deaths. Overall mortality rates have declined by 1% per year during the 1990s. There are currently over 9 million living Americans who have been diagnosed with cancer and the NIH estimates the direct medical costs of cancer as $60 billion per year.

Typical treatment modalities useful in the treatment of cancer include chemotherapy, radiotherapy and surgery (see, for example, Stockdale, 1998, "Principles of Cancer Subject Management", in *Scientific American: Medicine*, vol. 3, Rubenstein and Federman, eds., Chapter 12, Section IV). All of these approaches pose significant drawbacks for the subject. Surgery, for example, can be contraindicated due to the health of the subject or can be unacceptable to the subject. Additionally, surgery may not successfully remove all neoplastic tissue. Chemotherapy involves the administration of cytotoxic chemical agents which are associated with a broad spectrum of undesirable side effects, including alopecia, nausea and vomiting, hematoxicity, neurotoxicity, nephrotoxicity, cardiotoxicity and hepatotoxicity. In addition, cancer cells commonly develop resistance to most anticancer agents, thus rendering chemotherapy ineffective over time.

Radiation therapy, or radiotherapy as it is sometimes referred to, involves the treatment of cancer and other diseases using ionizing radiation. Ionizing radiation deposits energy that injures or destroys cells in targeted tissues by damaging their genetic material and subsequently interfering with a cell's ability to grow and/or replicate. Although radiation causes damage to both cancer cells and normal cells, the latter are better able to repair themselves and continue to function properly. Radiotherapy can be used to treat localized solid tumors, such as cancers of the skin, tongue, larynx, brain, breast, prostate, colon, uterus, lung, kidney, head and neck, and/or cervix. It can also be used to treat systemic forms of cancer such as the leukemias and lymphomas.

Radiotherapy is optimally effective when the targeted neoplastic tissue exhibits a higher sensitivity to the effects of radiation than neighboring normal tissue. In the absence of such differences in sensitivity, radiotherapy often elicits serious side effects.

Radiation responses of tumors vary as a function of histology, doubling time, oxygenation, availability of nutrients, repair capacity and other factors. Peters et al., *Int J Radiat. Biol.*, 1994, 66:523-529. Certain types of cancer are readily cured using ionizing radiation doses within normal tissue tolerances, while other types of cancer are not very responsive to radiation. Furthermore, radiation responses of tumors with the same histology may show considerable heterogeneity and reduce the therapeutic effects of the therapy. Weichselbaum et al, *Int. J. Radiat. Oncol. Biol. Phys.*, 1988, 14:907-912. Thus, a primary challenge facing radiotherapy is the differentiation between the more radiosensitive tumors vs. less radiosensitive tumors.

Investigations into the molecular bases underlying cellular radiation responses have provided dramatic mechanistic insight. Signal transduction pathways have been implicated to play important roles in cellular responses to ionizing radiation. Komberg et al., *Twenty-five years of the Nucleosome, Fundamental Particle of the Eukaryote Chromosome*, Cell Press 1999, 98:285-294. Induction of gene expression by these cascades under various conditions has been shown to result in cell cycle arrest, activation of DNA repair processes, and activation of programmed cell death (apoptosis). Meyn, *Cancer Res.*, 1995, 55:5991-6001, and Jackson et al., *Trends Biochem. Sci.*, 1995, 20:412-415. Disruption of critical signaling pathways in cancer cells results in enhanced cytotoxic effects following radiation exposure.

Histone acetylation and deacetylation play important roles in chromatin folding and maintenance. Komberg et al., Bjorklund et al., *Cell*, 1999, 96:759-767, and Struhl et al., *Cell*, 1998, 94:1-4. Acetylated chromatin is more open and has been implicated in the increased radiation sensitivities observed in some cell types. Oleinick et al., *Int. J. Radiat. Biol.*, 1994, 66:523-529. Furthermore, certain radiation-resistant human cancer cells treated with the histone deacetylase (HDAC) inhibitor, trichostatin A (TSA), were sensitized to the damaging effects of ionizing radiation. Thus, HDAC inhibitors may be useful as radiation sensitizing agents.

There is a significant need in the art for novel compounds, compositions, and methods that are useful for treating cancer or neoplastic disease with increased selectivity and decreased toxicity.

2.2 Neurological Diseases

Millions of people worldwide suffer from debilitating neurological diseases. Neurological diseases affect a vast number of humans of all ages (see Table 328-2 In: Wyngaarden and Smith, 1988, *Cecil Textbook of Medicine*, 18$^{th}$ Ed., W. B. Saunders Co., Philadelphia, pp.1750-1753). Each year in the United States alone, over 500,000 people experience a stroke, making it the third leading cause of death and the primary cause of disabililty. One in twenty people is afflicted with Alzheimer's disease by the age of 65, and almost 40 percent of the population have the disease by age 80. More than 600,000 people suffer from Parkinson's disease and over 200,000 from multiple sclerosis. Every year, greater than 10,000 people die from amyotrophic lateral sclerosis (ALS). The impact of neurological disease is not only devastating not only for patients, but also for their families Although considerable effort has been invested in the design of effective therapies, neurological diseases continue to threaten and lessen the qualitity of the lives of millions of people worldwide.

Accordingly, there is a need in the art for improved compounds, compositions, and methods useful for the treatment of neurological diseases.

The recitation of any reference in Section 2 of this application is not an admission that the reference is prior art to this application.

3. SUMMARY OF THE INVENTION

The present invention encompasses HDAC inhibitors, pharmaceutical compositions compositions comprising an HDAC inhibitor, and methods for treating cancer or a neurological disease comprising administering an HDAC inhibitor to a subject in need thereof.

Accordingly, in one embodiment, the invention provides compounds having the Formula (I):

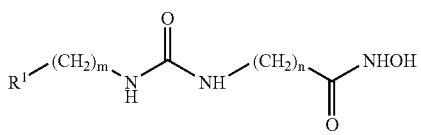

(I)

and pharmaceutically acceptable salts thereof,
wherein
R$^1$ is —C$_1$-C$_6$ alkyl, aryl, —C$_3$-C$_7$ cycloalkyl or -3- to 10-membered heterocycle, any of which may be unsubstituted or substituted with one or more —halo, —C$_1$-C$_6$ alkyl, —O —(C$_1$-C$_6$ alkyl), —OH, —CN, —COOR', —OC(O)R', NHR', N(R')$_2$, —NHC(O)R' or —C(O)NHR' groups wherein R$^1$ is —H or unsubstituted —C$_1$-C$_6$ alkyl; with the proviso that when n is 2, R$^1$ cannot be —C$_3$-C$_7$ cycloalkyl or -3- to 10-membered heterocycle;
m is an integer ranging from 1-10; and
n is an integer ranging from 1-10.

In another embodiment, the invention further provides compounds having the Formula (Ia):

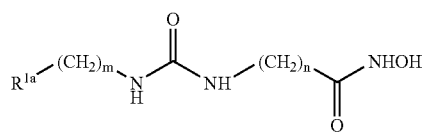

(Ia)

and pharmaceutically acceptable salts thereof,
wherein
R$^{1a}$ is —C$_1$-C$_6$ alkyl, aryl, —C$_3$-C$_7$ cycloalkyl or -3- to 10-membered heterocycle, any of which may be unsubstituted or substituted with one or more —halo, —C$_1$-C$_6$ alkyl, —O —(C$_1$-C$_6$ alkyl), —OH, —CN, —COOR', —OC(O)R', NHR', N(R')$_2$, —NHC(O)R' or —C(O)NHR' groups wherein R' is —H or unsubstituted —C$_1$-C$_6$ alkyl;
m is an integer ranging from 0-10; and
n is an integer ranging from 1-10.

In a further embodiment, the invention further provides compounds having the Formula (II):

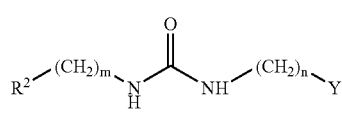

(II)

and pharmaceutically acceptable salts thereof,
wherein
Y is —C(O)CH$_2$SH or —NHC(O)CH$_2$SH;
R$^2$ is —C$_1$-C$_6$ alkyl, aryl, —C$_3$-C$_7$ cycloalkyl or -3- to 10-membered heterocycle, any of which may be unsubstituted or substituted with one or more —halo, —C$_1$-C$_6$ alkyl, —O —(C$_1$-C$_6$ alkyl), —OH, —CN, —COOR', —OC(O)R', NHR', N(R')$_2$, —NHC(O)R' or —C(O)NHR' groups wherein R' is —H or unsubstituted —C$_1$-C$_6$ alkyl;
m is an integer ranging from 0-10; and
n is an integer ranging from 1-10.

In still another embodiment, the invention further provides compounds having the Formula (III):

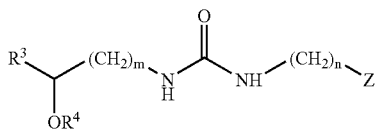

(III)

and pharmaceutically acceptable salts thereof,
wherein
Z is —C(O)NHOH, —C(O)CH$_2$SH or —NHC(O)CH$_2$SH;
R$^3$ is —C$_1$-C$_6$ alkyl, aryl, —C$_3$-C$_7$ cycloalkyl, -3- to 10-membered heterocycle, any of which may be unsubstituted or substituted with one or more —halo, —C$_1$-C$_6$ alkyl, —O —(C$_1$-C$_6$ alkyl), —OH, —CN, —COOR', —OC(O)R', NHR', N(R')$_2$, —NHC(O)R' or —C(O)NHR' groups wherein R' is —H or unsubstituted —C$_1$-C$_6$ alkyl;
R$^4$ is —H or —Si(R$^5$)$_3$;
each occurrence of R$^5$ is independently unsubstituted —C$_1$-C$_6$ alkyl;
m is an integer ranging from 0-10; and
n is an integer ranging from 1-10.

In yet another embodiment, the invention further provides compounds having the Formula (IV):

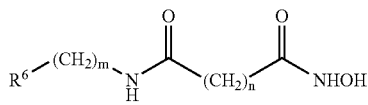

(IV)

and pharmaceutically acceptable salts thereof,
wherein
R$^6$ is —C$_1$-C$_6$ alkyl, aryl, —C$_3$-C$_7$ cycloalkyl or -3- to 10-membered heterocycle, any of which may be unsubstituted or substituted with one or more —halo, —C$_1$-C$_6$ alkyl, —O —(C$_1$-C$_6$ alkyl), —OH, —CN, —COOR', —OC(O)R', NHR', N(R')$_2$, —NHC(O)R' or —C(O)NHR' groups wherein R' is —H or unsubstituted —C$_1$-C$_6$ alkyl;
m is 1 or an integer ranging from 8-10; and
n is an integer ranging from 1-10.

In another embodiment, the invention further provides compounds having the Formula (IVa):

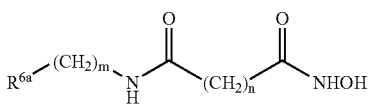

(IVa)

and pharmaceutically acceptable salts thereof,
wherein
R$^{6a}$ is —C$_1$-C$_6$ alkyl, aryl, —C$_3$-C$_7$ cycloalkyl or -3- to 10-membered heterocycle, any of which may be unsubstituted or substituted with one or more —halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' is —H or unsubstituted —$C_1$-$C_6$ alkyl;

m is an integer ranging from 0-10; and n is an integer ranging from 2-10.

In a further embodiment, the invention further provides compounds having the Formula (V):

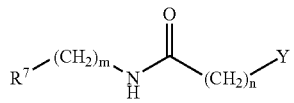

(V)

and pharmaceutically acceptable salts thereof,
wherein
Y is —C(O)CH$_2$SH or —NHC(O)CH$_2$SH;
$R^7$ is —$C_1$-$C_6$ alkyl, aryl, —$C_3$-$C_7$ cycloalkyl or -3- to 10-membered heterocycle, any of which may be unsubstituted or substituted with one or more —halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' is —H or unsubstituted —$C_1$-$C_6$ alkyl; with the proviso that when n is 2, $R^7$ cannot be —$C_3$-$C_7$ cycloalkyl or -3- to 10-membered heterocycle;
m is an integer ranging from 0-10; and
n is an integer ranging from 1-10.

In another embodiment, the invention further provides compounds having the Formula (VI):

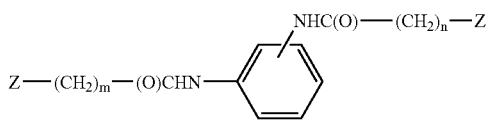

(VI)

and pharmaceutically acceptable salts thereof,
wherein
each Z is independently —C(O)NHOH, —C(O)CH$_2$SH or —NHC(O)CH$_2$SH, with the proviso that when both Z groups are —C(O)NHOH, the phenyl group of said compound of formula (VI) is either ortho or meta substituted;
m is an integer ranging from 1-10; and
n is an integer ranging from 1-10.

In yet another embodiment, the invention further provides compounds having the Formula (VII):

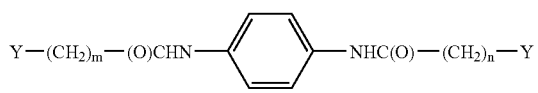

(VII)

and pharmaceutically acceptable salts thereof,
wherein
each Y is independently —C(O)CH$_2$SH or —NHC(O)CH$_2$SH;
m is an integer ranging from 1-10; and
n is an integer ranging from 1-10.

In a further embodiment, the invention further provides compounds having the Formula (VIII):

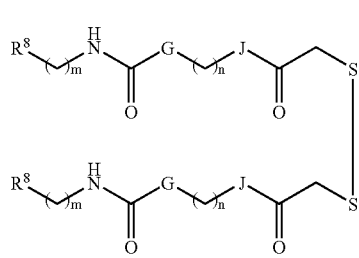

(VIII)

and pharmaceutically acceptable salts thereof,
wherein:
each $R^8$ is independently —$C_1$-$C_6$ alkyl, aryl, —$C_3$-$C_7$ cycloalkyl or -3- to 10-membered heterocycle, any of which may be unsubstituted or substituted with one or more —halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' is —H or unsubstituted —$C_1$-$C_6$ alkyl;
each G is independently —NH— or —CH$_2$—;
each J is independently —NH— or —CH$_2$—;
each m is independently an integer ranging from 1-10; and
each n is independently an integer ranging from 1-10.

In a further embodiment, the invention further provides compounds having the Formula (IX):

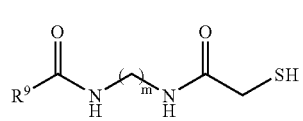

(IX)

and pharmaceutically acceptable salts thereof,
wherein
$R^9$ is phenyl, which can be unsubstituted or substituted with one or more —halo, —$C_1$-$C_6$alkyl, —O—($C_1$-$C_6$ alkyl), —OH, —CN, —COOR', —OC(O)R', NHR', N(R')$_2$, —NHC(O)R' or —C(O)NHR' groups wherein R' is —H or unsubstituted —$C_1$-$C_6$ alkyl; and
m is an integer ranging from 2-10.

The invention also provides pharmaceutical compositions comprising the compound of Formula (I), (II), (III), (IV), (V), (VI), (VII), (VIII) or (IX), or a pharmaceutically acceptable salt thereof, in an amount sufficient to treat said cancer, and a pharmaceutically acceptable carrier or vehicle. The compositions are useful for treating cancer.

The present invention further provides methods for increasing the sensitivity of a cancer cell to the cytotoxic effects of radiotherapy, said method comprising contacting said cell with the compound or pharmaceutically acceptable salt of the compound of Formula (I), (Ia), (II), (III), (IV), (IVa), (V), (VI), (VII), (VIII) or (IX), in an amount sufficient to increase the sensitivity of said cell to the cytotoxic effects of radiotherapy.

The invention also provides methods for treating cancer, said methods comprising administering to a subject in need thereof the compound or pharmaceutically acceptable salt of the compound of Formula (I), (II), (III), (IV), (V), (VI), (VII), (VIII) or (IX), in an amount sufficient to treat said cancer.

The invention further provides methods for treating cancer, said methods comprising:
(a) administering to a subject in need thereof, the compound or pharmaceutically acceptable salt of the compound of Formula (I), (Ia), (II), (III), (IV), (IVa), (V), (VI), (VII), (VIII) or (IX), in an amount sufficient to sensitize a cancer cell to the cytotoxic effects of radiotherapy; and
(b) administering to said subject an amount of radiotherapy sufficient to treat said cancer.

The present invention also provides a method for treating a neurological disease, said method comprising administering to a subject in need thereof the compound or pharmaceutically acceptable salt of the compound of Formula (I), (Ia), (II), (III), (IV), (IVa), (V), (VI), (VII), (VIII) or (IX), in an amount sufficient to treat said neurological disease.

The present invention also provides kits comprising a container which contains the compound or pharmaceutically acceptable salt of the compound of Formula (I), (Ia), (II), (III), (IV), (IVa), (V), (VI), (VII), (VIII) or (IX).

The details of the invention are set forth in the accompanying description below. Although any methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents, patent applications and publications cited in this specification are incorporated herein by reference for all purposes.

4. BRIEF DESCRIPTION OF THE DRAWINGS

FIG. 1 illustrates the inhibitory effect of selected compounds of the invention on HDAC acitivity in HeLa nuclear cell extracts. Data is expressed as arbitrary fluorescence units (AFU)/μM obtained with the observed range of values obtained in the enzyme assays used in a series of dilutions for a standard curve. Data is shown for a blank sample (no enzyme), a control sample (no inhibitor), the known compound MD83A (as a negative control) at 3 μM, the known HDAC inhibitor TSA at 0.5 μM and 5 μM, the known HDAC inhibitor SAHA at 1 μM and 5 μM, and Compounds of the Invention 2, 3, 5, 6, 7, 8, 9, 10, 11, 21, 22, 23, 24 and 25, each at 5 μM.

5. DETAILED DESCRIPTION OF THE INVENTION 5.1 Definitions

The term "$C_1$-$C_6$ alkyl" as used herein refers to a straight or branched chain, saturated or unsaturated hydrocarbon having from 1 to 6 carbon atoms. Representative $C_1$-$C_6$ alkyl groups include, but are not limited to methyl, ethyl, propyl, isopropyl, butyl, sec-butyl, tert-buty, pentyl, isopentyl, neopentyl, hexyl, isohexyl, neohexyl, ethylenyl, propylenyl, 1-butenyl, 2-butenyl, 1-pentenyl, 2-pentenyl, 1-hexenyl, 2-hexenyl, 3-hexenyl, acetylenyl, pentynyl, 1-butynyl, 2-butynyl, 1-pentynyl, 2-pentynyl, 1-hexynyl, 2-hexynyl and 3-hexynyl. A $C_1$-$C_6$ alkyl group may be unsubstituted or substituted with one or more of the following groups: —halo, —$C_1$-$C_6$alkyl, —O—($C_1$-$C_6$ alkyl), —OH, —CN, —COOR', —OC(O)R', NHR', N(R')$_2$, —NHC(O)R' or —C(O)NHR' groups wherein R' is —H or unsubstituted —$C_1$-$C_6$ alkyl.

The term "aryl" as used herein refers to a phenyl group or a naphthyl group. An aryl group may be unsubstituted or substituted with one or more of the following groups: —halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' is —H or unsubstituted —$C_1$-$C_6$ alkyl.

The phrase "Compounds of the Invention" as used herein refers to a compound of Formula (I), (Ia), (II), (III), (IV), (IVa), (V), (VI), (VII), (VIII) or (IX) or a pharmaceutically acceptable salt thereof. In some instances, it is possible for a Compound of the Invention to have one or more chiral centers. In these instances, it is to be understood that the invention encompasses all possible stereoisomers of these compounds.

The term "$C_3$-$C_7$ cycloalkyl" as used herein is a 3-, 4-5-, 6- or 7-membered saturated or unsaturated non-aromatic carbocyclic ring. Representative $C_3$-$C_7$ cycloalkyls include, but are not limited to, cyclopropyl, cyclobutyl, cyclopentyl, cyclopentadienyl, cyclohexyl, cyclohexenyl, cycloheptyl, cycloheptanyl, 1,3-cyclohexadienyl, -1,4-cyclohexadienyl, -1,3-cycloheptadienyl, and -1,3,5-cycloheptatrienyl. A $C_3$-$C_7$ cycloalkyl group may be unsubstituted or substituted with one or more of the following groups: —halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' is —H or unsubstituted —$C_1$-$C_6$ alkyl.

The term "halo" as used herein refers to —F, —Cl, —Br or —I.

As used herein, a "-3- to 10-membered heterocycle" is a 3- to 10-membered aromatic or nonaromatic monocyclic or bicyclic ring of carbon atoms and from 1 to 4 heteroatoms selected from oxygen, nitrogen and sulfur. Examples of 3- to 10-membered heterocycles include, but are not limited to, aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzthiazolyl, thiophenyl, pyrazolyl, triazolyl, benzodiazolyl, benzotriazolyl, pyrimidinyl, isoindolyl and indazolyl. A -3- to 10-membered heterocycle group may be unsubstituted or substituted with one or more of the following groups: —halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' is —H or unsubstituted —$C_1$-$C_6$ alkyl.

The Compounds of the Invention can be formulated as pharmaceutically acceptable salts. The phrase "pharmaceutically acceptable salt," as used herein, refers to a pharmaceutically acceptable organic or inorganic acid or base salt of an organic chemical compound. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. The counterion may be any organic or inorganic moiety that stabilizes the charge on the parent compound. Furthermore, a pharmaceutically acceptable salt may have more than one charged atom in its structure. In this instance the pharmaceutically acceptable salt can have multiple counterions. Hence, a pharmaceutically acceptable salt can have one or more charged atoms and/or one or more counterions.

As used herein, the term "purified" means that when isolated (e.g., from other components of a synthetic organic chemical reaction mixture), the isolate contains at least 30%, at least 35%, at least 40%, at least 45%, at least 50%, at least 55%, at least 60%, at least 65%, at least 70%, at least 75%, at least 80%, at least 85%, at least 90%, at least 95% or at least 98% of a Compound of the Invention by weight of the isolate. In a preferred embodiment, the isolate contains at least 95% of a Compound of the Invention by weight of the isolate.

The following abbreviations are used herein and have the indicated definitions:

DMSO is dimethylsulfoxide, DTT is dithiothreitol, EDCI is 1-(3-dimethylaminopropyl)-3-ethylcarbodiimide hydrochloride, EDTA is ethylenediaminetetraacetic acid, Et$_3$N is triethylamine, EtOAc is ethyl acetate, HDAC is histone deacetylase, HEPES is N-2-hydroxyethylpiperazine-N'-2-ethanesulfonic acid, MeOH is methanol, MS is mass spectrometry, NMR is nuclear magnetic resonance, PBS is phosphate buffered saline, PDV is, SAHA is suberoylanilide hydroxamic acid, TBS is tert-butyldimethylsilyl, THF is tetrahydrofuran, Tr is trityl (triphenylmethyl), and TSA is trichostatin A (7-(4-(dimethylamino)phenyl)-n-hydroxy-4,6-dimethyl-7-oxo-2,4-heptadienamide).

5.2 The Compounds of the Invention

5.2.1 The Compounds of Formula (I)

As stated above, the present invention encompasses compounds having the Formula (I)

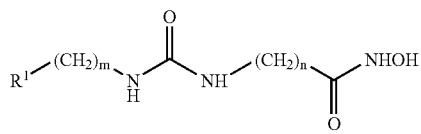

(I)

and pharmaceutically acceptable salts thereof,
wherein
R$^1$ is —C$_1$-C$_6$ alkyl, aryl, —C$_3$-C$_7$ cycloalkyl or -3- to 10-membered heterocycle, any of which may be unsubstituted or substituted with one or more of the following groups: —halo, —C$_1$-C$_6$ alkyl, —O—(C$_1$-C$_6$ alkyl), —OH, —CN, —COOR', —OC(O)R', NHR', N(R')$_2$, —NHC(O)R' or —C(O)NHR' groups wherein R' is —H or unsubstituted —C$_1$-C$_6$ alkyl; with the proviso that when n is 2, R$^1$ cannot be —C$_3$-C$_7$ cycloalkyl or -3- to 10-membered heterocycle;
m is an integer ranging from 1-10; and
n is an integer ranging from 1-10.

A first subclass of the compounds of Formula (I) is that wherein R$^1$ is phenyl.

A second subclass of the compounds of Formula (I) is that wherein n is an integer ranging from 1 to 5.

A third subclass of the compounds of Formula (I) is that wherein m is 2.

A fourth subclass of the compounds of Formula (I) is that wherein m is 1 and R$^1$ is 4-(N,N-dimethylamino)phenyl.

Illustrative Compounds of Formula (I) include the compounds listed below:

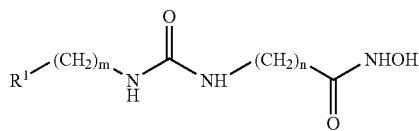

| Compound No. | R$^1$ | m | n |
|---|---|---|---|
| 1 | Phenyl | 2 | 3 |
| 2 | 4-N(CH$_3$)$_2$-Phenyl | 1 | 3 |
| 3 | 4-N(CH$_3$)$_2$-Phenyl | 1 | 4 |
| 4 | 4-N(CH$_3$)$_2$-Phenyl | 1 | 5 |
| 5 | 4-N(CH$_3$)$_2$-Phenyl | 1 | 6 |
| 6 | 4-N(CH$_3$)$_2$-Phenyl | 1 | 7 | and pharmaceutically acceptable salts thereof.

The present invention also provides pharmaceutical compositions comprising the compound of Formula (I) or a pharmaceutically acceptable salt thereof, and a pharmaceutically acceptable carrier or vehicle.

The invention also provides a method for treating cancer, said method comprising administering to a subject in need thereof the compound of Formula (I) or a pharmaceutically acceptable salt thereof, in an amount sufficient to treat said cancer.

The invention further provides method for increasing the sensitivity of a cancer cell to the cytotoxic effects of radiotherapy, said method comprising contacting said cell with the compound of Formula (I) in an amount sufficient to increase the sensitivity of said cell to the cytotoxic effects of radiotherapy.

The invention also provides a method for treating cancer, said method comprising the steps of:
(a) administering to a subject in need thereof the compound of Formula (I) or a pharmaceutically acceptable salt thereof, in an amount sufficient to sensitize a cancer cell to the cytotoxic effects of radiotherapy; and
(b) administering to said subject an amount of radiotherapy sufficient to treat said cancer.

The invention also provides a method for treating a neurological disease, said method comprising administering to a subject in need thereof the compound of Formula (I), or a pharmaceutically acceptable salt thereof, in an amount sufficient to treat said neurological disease.

5.2.2 The Compounds of Formula (Ia)

As stated above, the present invention encompasses compounds having the Formula (Ia):

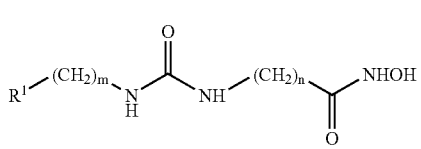

(Ia)

and pharmaceutically acceptable salts thereof, wherein
R¹ is —$C_1$-$C_6$ alkyl, aryl, —$C_3$-$C_7$ cycloalkyl or -3- to 10-membered heterocycle, any of which may be unsubstituted or substituted with one or more of the following groups: —halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' is —H or unsubstituted —$C_1$-$C_6$ alkyl;

m is an integer ranging from 0-10; and n is an integer ranging from 1-10.

Illustrative examples of compounds of Formula (Ia) include the compounds listed below:

$$R^1 \diagup (CH_2)_m \diagdown \underset{H}{N} \diagdown \underset{\underset{O}{\|}}{C} \diagdown NH \diagup (CH_2)_n \diagdown \underset{\underset{O}{\|}}{C} \diagdown NHOH$$

| Compound No. | R¹ | m | n |
|---|---|---|---|
| 7 | 4-N(CH$_3$)$_2$-Phenyl | 0 | 6 |
| 8 | Adamantyl | 0 | 5 | and pharmaceutically acceptable salts thereof.

The invention further provides a method for increasing the sensitivity of a cancer cell to the cytotoxic effects of radiotherapy, said method comprising contacting said cell with the compound of Formula (Ia) or a pharmaceutically acceptable salt thereof, in an amount sufficient to increase the sensitivity of said cell to the cytotoxic effects of radiotherapy.

The invention also provides a method for treating cancer, said method comprising the steps of:
(a) administering to a subject in need thereof the compound of Formula (Ia) or a pharmaceutically acceptable salt thereof, in an amount sufficient to sensitize a cancer cell to the cytotoxic effects of radiotherapy; and
(b) administering to said subject an amount of radiotherapy sufficient to treat said cancer.

The invention also provides a method for treating a neurological disease, said method comprising administering to a subject in need thereof, the compound of Formula (Ia) or a pharmaceutically acceptable salt thereof, in an amount sufficient to treat said neurological disease.

5.2.3 The Compounds of Formula (II)

As stated above, the present invention encompasses compounds having the Formula (II)

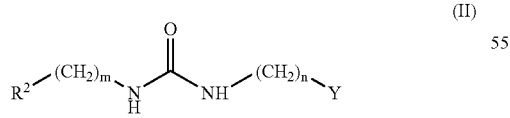

and pharmaceutically acceptable salts thereof,
wherein
Y is —C(O)CH$_2$SH or —NHC(O)CH$_2$SH;
R² is —$C_1$-$C_6$ alkyl, aryl, —$C_3$-$C_7$ cycloalkyl or -3- to 10-membered heterocycle, any of which may be unsubstituted or substituted with one or more of the following groups: —halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' is —H or unsubstituted —$C_1$-$C_6$ alkyl;

m is an integer ranging from 0-10; and n is an integer ranging from 1-10.

A first subclass of the compounds of Formula (II) is that wherein m is 1.

A second subclass of the compounds of Formula (II) is that wherein R² is 4-(N,N-dimethylamino)phenyl.

A third subclass of the compounds of Formula (II) is that wherein m is 1 and R² is 4-(N,N-dimethylamino)phenyl.

Illustrative Compounds of Formula (II) include the compounds listed below:

$$R^2 \diagup (CH_2)_m \diagdown \underset{H}{N} \diagdown \underset{\underset{O}{\|}}{C} \diagdown NH \diagup (CH_2)_n \diagdown Y$$

| Compound No. | R² | Y | m | n |
|---|---|---|---|---|
| 9 | Phenyl | —NHC(O)CH$_2$SH | 0 | 5 |
| 10 | Phenyl | —NHC(O)CH$_2$SH | 0 | 6 |
| 11 | Phenyl | —NHC(O)CH$_2$SH | 1 | 5 |
| 12 | 4-N(CH$_3$)$_2$-Phenyl | —NHC(O)CH$_2$SH | 1 | 6 |
| 13 | Phenyl | —NHC(O)CH$_2$SH | 0 | 6 | and pharmaceutically acceptable salts thereof.

The present invention also provides pharmaceutical compositions comprising the compound of Formula (II) or a pharmaceutically acceptable salt thereof, and a pharmaceutically acceptable carrier or vehicle.

The invention also provides a method for increasing the sensitivity of a cancer cell to the cytotoxic effects of radiotherapy, said method comprising contacting said cell with the compound or a pharmaceutically acceptable salt of the compound of Formula (II) effective to increase the sensitivity of said cell to the cytotoxic effects of radiotherapy.

The invention also provides a method for treating cancer, said method comprising administering to a subject in need thereof the compound of Formula (II) or a pharmaceutically acceptable salt thereof, in an amount sufficient to treat said cancer.

The invention also provides a method for treating cancer, said method comprising the steps of:
(a) administering to a subject in need thereof the compound of Formula (II) or a pharmaceutically acceptable salt thereof, in an amount sufficient to sensitize a cancer cell to the cytotoxic effects of radiotherapy; and
(b) administering to said subject an amount of radiotherapy sufficient to treat said cancer.

The invention also provides a method for treating a neurological disease, said method comprising administering to a subject in need thereof the compound of Formula (II) or a pharmaceutically acceptable salt thereof, in an amount sufficient to treat said neurological disease.

5.2.4 The Compounds of Formula (III)

As stated above, the present invention encompasses compounds having the Formula (III)

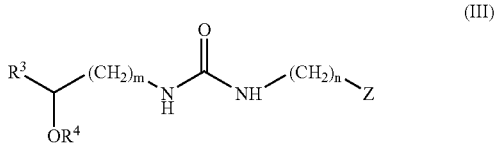

(III)

and pharmaceutically acceptable salts thereof,
wherein
Z is —C(O)NHOH, —C(O)CH$_2$SH or —NHC(O)CH$_2$SH;
$R^3$ is —C$_1$-C$_6$ alkyl, aryl, —C$_3$-C$_7$ cycloalkyl, -3- to 10-membered heterocycle, any of which may be unsubstituted or substituted with one or more of the following groups: —halo, —C$_1$-C$_6$alkyl, —O—(C$_1$-C$_6$alkyl), —OH, —CN, —COOR', —OC(O)R', NHR',N(R')$_2$, —NHC(O)R' or —C(O)NHR' groups wherein R' is —H or unsubstituted —C$_1$-C$_6$ alkyl;
$R^4$ is —H or —Si(R$^5$)$_3$;
each occurrence of $R^5$ is independently unsubstituted —C$_1$-C$_6$ alkyl;
m is an integer ranging from 0-10; and
n is an integer ranging from 1-10.

A first subclass of the compounds of Formula (III) is that wherein wherein m is 2.

A second subclass of the compounds of Formula (III) is that wherein wherein n is 2 or 3.

A third subclass of the compounds of Formula (III) is that wherein wherein $R^4$ is —H.

A fourth subclass of the compounds of Formula (III) is that wherein $R^3$ is phenyl.

Illustrative examples of Compounds of Formula (III) include the compounds listed below:

| Compound No. | R$^3$ | R$^4$ | Z | m | n |
|---|---|---|---|---|---|
| 14 | Phenyl | H | —C(O)NHOH | 1 | 2 |
| 15 | Phenyl | H | —C(O)NHOH | 1 | 3 |
| 16 | Phenyl | —Si(CH$_3$)$_2$(t-butyl) | —C(O)NHOH | 1 | 3 | and pharmaceutically acceptable salts thereof.

The present invention also provides pharmaceutical compositions comprising the compound of Formula (III) or a pharmaceutically acceptable salt thereof, and a pharmaceutically acceptable carrier or vehicle.

The invention also provides a method for increasing the sensitivity of a cancer cell to the cytotoxic effects of radiotherapy, said method comprising contacting said cell with the compound of Formula (III) or a pharmaceutically salt thereof, in an amount sufficient to increase the sensitivity of said cell to the cytotoxic effects of radiotherapy.

The invention also provides a method for treating cancer, said method comprising administering to a subject in need thereof the compound of Formula (III) or a pharmaceutically acceptable salt thereof, in an amount sufficient to treat said cancer.

The invention also provides a method for treating cancer, said method comprising the steps of:
(a) administering to a subject in need thereof the compound of Formula (III) or a pharmaceutically acceptable salt thereof, in an amount sufficient to sensitize a cancer cell to the cytotoxic effects of radiotherapy; and
(b) administering to said subject an amount of radiotherapy sufficient to treat said cancer.

The invention also provides a method for treating a neurological disease, said method comprising administering to a subject in need thereof the compound of Formula (III) or a pharmaceutically acceptable salt thereof, in an amount sufficient to treat said neurological disease.

5.2.5 The Compounds of Formula (IV)

As stated above, the present invention encompasses compounds having the Formula (IV):

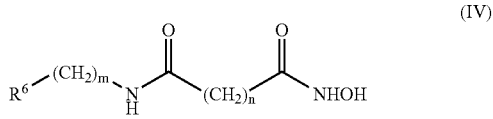

(IV)

and pharmaceutically acceptable salts thereof,
wherein
$R^6$ is —C$_1$-C$_6$ alkyl, aryl, —C$_3$-C$_7$ cycloalkyl or -3- to 10-membered heterocycle, any of which may be unsubstituted or substituted with one or more of the following groups: —halo, —C$_1$-C$_6$ alkyl, —O—(C$_1$-C$_6$ alkyl), —OH, —CN, —COOR', —OC(O)R', NHR', N(R')$_2$, —NHC(O)R' or —C(O)NHR' groups wherein R' is —H or unsubstituted —C$_1$-C$_6$ alkyl;
m is 1 or an integer ranging from 8-10; and
n is an integer ranging from 1-10.

The present invention also provides pharmaceutical compositions comprising a compound of Formula (IV) or a pharmaceutically acceptable salt thereof, and a pharmaceutically acceptable carrier or vehicle.

A method for increasing the sensitivity of a cancer cell to the cytotoxic effects of radiotherapy, said method comprising contacting said cell with the compound of Formula (IV) or pharmaceutically salt thereof, effective to increase the sensitivity of said cell to the cytotoxic effects of radiotherapy.

The invention also provides a method for treating cancer, said method comprising administering to a subject in need thereof the compound of Formula (IV) or a pharmaceutically acceptable salt thereof, in an amount sufficient to treat said cancer.

The invention also provides a method for treating cancer, said method comprising the steps of:
(a) administering to a subject in need thereof the compound of Formula (IV) or a pharmaceutically acceptable salt thereof, in an amount sufficient to sensitize a cancer cell to the cytotoxic effects of radiotherapy; and
(b) administering to said subject an amount of radiotherapy sufficient to treat said cancer.

The invention also provides a method for treating a neurological disease, said method comprising administering to a subject in need thereof the compound of Formula (IV) or a pharmaceutically acceptable salt thereof, in an amount sufficient to treat said neurological disease.

5.2.6 The Compounds of Formula (IVa)

As stated above, the present invention encompasses compounds having the Formula (IVa):

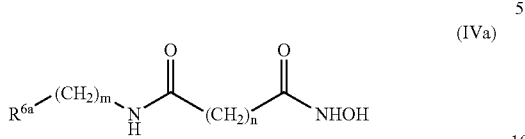
(IVa)

and pharmaceutically acceptable salts thereof,
wherein
$R^{6a}$ is —$C_1$-$C_6$ alkyl, aryl, —$C_3$-$C_7$ cycloalkyl or -3- to 10-membered heterocycle, any of which may be unsubstituted or substituted with one or more of the following groups: —halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' is —H or unsubstituted —$C_1$-$C_6$ alkyl;
m is an integer ranging from 0-10; and
n is an integer ranging from 2-10.

An illustrative example of a Compound of Formula (IVa) is the compound having the formula:

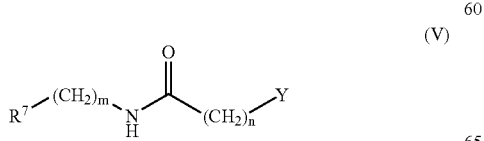

| Compound No. | $R^{6a}$ | m | n |
|---|---|---|---|
| 17 | Adamantyl | 0 | 5 | or a pharmaceutically acceptable salt thereof.

A method for increasing the sensitivity of a cancer cell to the cytotoxic effects of radiotherapy, said method comprising contacting said cell with the compound of Formula (IVa) or pharmaceutically salt thereof, effective to increase the sensitivity of said cell to the cytotoxic effects of radiotherapy.

The invention also provides a method for treating cancer, said method comprising the steps of:

(a) administering to a subject in need thereof the compound of Formula (IVa) or a pharmaceutically acceptable salt thereof, in an amount sufficient to sensitize a cancer cell to the cytotoxic effects of radiotherapy; and (b) administering to said subject an amount of radiotherapy sufficient to treat said cancer.

The invention also provides a method for treating a neurological disease, said method comprising administering to a subject in need thereof the compound of Formula (IVa) or a pharmaceutically acceptable salt thereof, in an amount sufficient to treat said neurological disease.

5.2.7 The Compounds of Formula (V)

As stated above, the present invention encompasses compounds having the Formula (V):

$$R^7 \underset{(CH_2)_m}{\diagdown} \underset{H}{N} \underset{\parallel}{\overset{O}{C}} (CH_2)_n Y \qquad (V)$$

and pharmaceutically acceptable salts thereof,
wherein
Y is —C(O)CH$_2$SH or —NHC(O)CH$_2$SH;
$R^7$ is —$C_1$-$C_6$ alkyl, aryl, —$C_3$-$C_7$ cycloalkyl or -3- to 10-membered heterocycle, any of which may be unsubstituted or substituted with one or more of the following groups: —halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' is —H or unsubstituted —$C_1$-$C_6$ alkyl; with the proviso that when n is 2, $R^7$ cannot be —$C_3$-$C_7$ cycloalkyl or -3- to 10-membered heterocycle;
m is an integer ranging from 0-10; and
n is an integer ranging from 1-10.

The present invention also provides pharmaceutical compositions comprising the compound of Formula (V) or a pharmaceutically acceptable salt thereof, and a pharmaceutically acceptable carrier or vehicle.

A method for increasing the sensitivity of a cancer cell to the cytotoxic effects of radiotherapy, said method comprising contacting said cell with the compound of Formula (V) or pharmaceutically salt thereof, effective to increase the sensitivity of said cell to the cytotoxic effects of radiotherapy.

The invention also provides a method for treating cancer, said method comprising administering to a subject in need thereof the compound of Formula (V) or a pharmaceutically acceptable salt thereof, in an amount sufficient to treat said cancer.

The invention also provides a method for treating cancer, said method comprising the steps of:

(a) administering to a subject in need thereof the compound of Formula (V) or a pharmaceutically acceptable salt thereof, in an amount sufficient to sensitize a cancer cell to the cytotoxic effects of radiotherapy; and (b) administering to said subject an amount of radiotherapy sufficient to treat said cancer.

The invention also provides a method for treating a neurological disease, said method comprising administering to a subject in need thereof the compound of Formula (V) or a pharmaceutically acceptable salt thereof, in an amount sufficient to treat said neurological disease.

5.2.8 The Compounds of Formula (VI)

As stated above, the present invention encompasses compounds having the Formula (VI):

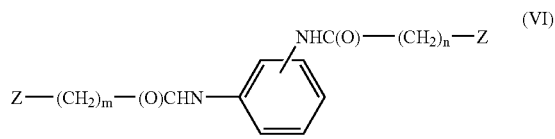
(VI)

and pharmaceutically acceptable salts thereof,
wherein
each Z is independently —C(O)NHOH, —C(O)CH$_2$SH or —NHC(O)CH$_2$SH, with the proviso that when both Z groups are —C(O)NHOH, the phenyl group of said compound of formula (VI) is either ortho or meta substituted;
m is an integer ranging from 1-10; and
n is an integer ranging from 1-10.

A subclass of the compounds of Formula (VI) is that wherein each occurrence of Z is —C(O)NHOH.

An illustrative Compound of Formula (VI) is the compound shown below:

| Z—(CH₂)ₙ—(O)CHN |
| Z—(CH₂)ₘ—(O)CHN— (phenyl) |

| Compound No. | Z | m | n |
|---|---|---|---|
| 18 | —C(O)NHOH | 6 | 6 | or a pharmaceutically acceptable salt thereof.

The present invention also provides pharmaceutical compositions comprising the compound of Formula (VI) or a pharmaceutically acceptable salt thereof, and a pharmaceutically acceptable carrier or vehicle.

A method for increasing the sensitivity of a cancer cell to the cytotoxic effects of radiotherapy, said method comprising contacting said cell with the compound of Formula (VI) or pharmaceutically salt thereof, effective to increase the sensitivity of said cell to the cytotoxic effects of radiotherapy.

The invention also provides a method for treating cancer, said method comprising administering to a subject in need thereof the compound of Formula (VI) or a pharmaceutically acceptable salt thereof, in an amount sufficient to treat said cancer.

The invention also provides a method for treating cancer, said method comprising the steps of:
(a) administering to a subject in need thereof the compound of Formula (VI) or a pharmaceutically acceptable salt thereof, in an amount sufficient to sensitize a cancer cell to the cytotoxic effects of radiotherapy; and
(b) administering to said subject an amount of radiotherapy sufficient to treat said cancer.

The invention also provides a method for treating a neurological disease, said method comprising administering to a subject in need thereof the compound of Formula (VI) or a pharmaceutically acceptable salt thereof, in an amount sufficient to treat said neurological disease.

5.2.9 The Compounds of Formula (VII)

As stated above, the present invention encompasses compounds having the Formula (VII):

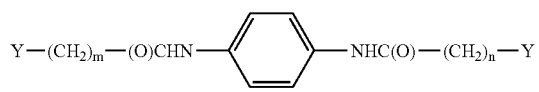

(VII)

and pharmaceutically acceptable salts thereof,
wherein
each Y is independently —C(O)CH₂SH or —NHC(O)CH₂SH;
m is an integer ranging from 1-10; and
n is an integer ranging from 1-10.

The present invention also provides a method for increasing the sensitivity of a cancer cell to the cytotoxic effects of radiotherapy, said method comprising contacting said cell with the compound of Formula (VII) or pharmaceutically salt thereof, effective to increase the sensitivity of said cell to the cytotoxic effects of radiotherapy.

The invention also provides a method for treating cancer, said method comprising administering to a subject in need thereof the compound of Formula (VII) or a pharmaceutically acceptable salt thereof, in an amount sufficient to treat said cancer.

The invention also provides a method for treating cancer, said method comprising the steps of:
(a) administering to a subject in need thereof the compound of Formula (VII) or a pharmaceutically acceptable salt thereof, in an amount sufficient to sensitize a cancer cell to the cytotoxic effects of radiotherapy; and
(b) administering to said subject an amount of radiotherapy sufficient to treat said cancer.

The invention also provides a method for treating a neurological disease, said method comprising administering to a subject in need thereof the compound of Formula (VII) or a pharmaceutically acceptable salt thereof, in an amount sufficient to treat said neurological disease.

5.2.10 The Compounds of Formula (VIII)

As stated above, the present invention encompasses compounds having the Formula (VIII):

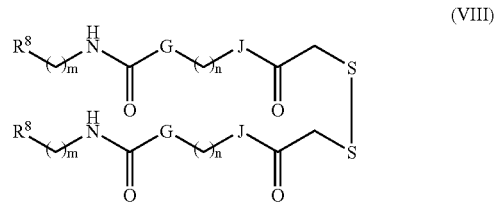

(VIII)

and pharmaceutically acceptable salts thereof,
wherein
each $R^8$ is independently —$C_1$-$C_6$ alkyl, aryl, —$C_3$-$C_7$ cycloalkyl or -3- to 10-membered heterocycle, any of which may be unsubstituted or substituted with one or more of the following groups: —halo, —$C_1$-$C_6$ alkyl, —O—($C_1$-$C_6$ alkyl), —OH, —CN, —COOR', —OC(O)R', NHR', N(R')₂, —NHC(O)R' or —C(O)NHR' groups wherein R' is —H or unsubstituted —$C_1$-$C_6$ alkyl;
each G is independently —NH— or —CH₂—;
each J is independently —NH— or —CH₂—;
each m is independently an integer ranging from 1-10; and
each n is independently an integer ranging from 1-10.

Illustrative examples of Compounds of Formula (VIII) include the compounds listed below:

| Compound No. | R⁸ | G | J | m | n |
|---|---|---|---|---|---|
| 19 | Phenyl | —NH— | —NH— | 0 | 6 |
| 20 | 4-N(CH₃)₂-Phenyl | —NH— | —NH— | 1 | 6 | and pharmaceutically acceptable salts thereof.

The present invention also provides pharmaceutical compositions comprising the compound of Formula (VIII) or a pharmaceutically acceptable salt thereof, and a pharmaceutically acceptable carrier or vehicle.

A method for increasing the sensitivity of a cancer cell to the cytotoxic effects of radiotherapy, said method comprising contacting said cell with the compound of Formula (VIII) or pharmaceutically salt thereof, effective to increase the sensitivity of said cell to the cytotoxic effects of radiotherapy.

The invention also provides a method for treating cancer, said method comprising administering to a subject in need thereof the compound of Formula (VIII) or a pharmaceutically acceptable salt thereof, in an amount sufficient to treat said cancer.

The invention also provides a method for treating cancer, said method comprising the steps of:
(a) administering to a subject in need thereof the compound of Formula (VIII) or a pharmaceutically acceptable salt thereof, in an amount sufficient to sensitize a cancer cell to the cytotoxic effects of radiotherapy; and
(b) administering to said subject an amount of radiotherapy sufficient to treat said cancer.

The invention also provides a method for treating a neurological disease, said method comprising administering to a subject in need thereof the compound of Formula (VIII) or a pharmaceutically acceptable salt thereof, in an amount sufficient to treat said neurological disease.

5.2.11 The Compounds of Formula (IX)

As stated above, the present invention encompasses compounds having the Formula (IX)

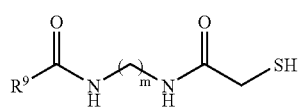

(IX)

and pharmaceutically acceptable salts thereof,
wherein
$R^9$ is phenyl, which can be unsubstituted or substituted with one or more of the following groups: —halo, —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' is —H or unsubstituted —$C_1$-$C_6$ alkyl; and
m is an integer ranging from 2-10.

A first subclass of the compounds of Formula (IX) is that wherein m is 5.

A second subclass of the compounds of Formula (IX) is that wherein m is 6.

A third subclass of the compounds of Formula (IX) is that wherein $R^9$ is -phenyl.

A fourth subclass of the compounds of Formula (IX) is that wherein $R^9$ is –4-N(CH$_3$)$_2$-phenyl.

A fifth subclass of the compounds of Formula (IX) is that wherein $R^9$ is –4-biphenyl.

Illustrative examples of Compounds of Formula (IX) include the compounds listed below:

| Compound No. | $R^9$ |
|---|---|
| 21 | -phenyl |
| 22 | -4-N(CH$_3$)$_2$-phenyl |
| 23 | -4-biphenyl |
| 24 | -4-N(CH$_3$)$_2$-phenyl |
| 25 | -phenyl | and pharmaceutically acceptable salts thereof.

The present invention also provides pharmaceutical compositions comprising the compound of Formula (IX) or a pharmaceutically acceptable salt thereof, and a pharmaceutically acceptable carrier or vehicle.

A method for increasing the sensitivity of a cancer cell to the cytotoxic effects of radiotherapy, said method comprising contacting said cell with the compound of Formula (IX) or pharmaceutically salt thereof, in an amount sufficient to increase the sensitivity of said cell to the cytotoxic effects of radiotherapy.

The invention also provides a method for treating cancer, said method comprising administering to a subject in need thereof the compound of Formula (IX) or a pharmaceutically acceptable salt thereof, in an amount sufficient to treat said cancer.

The invention also provides a method for treating cancer, said method comprising the steps of:
(a) administering to a subject in need thereof the compound of Formula (IX) or a pharmaceutically acceptable salt thereof, in an amount sufficient to sensitize a cancer cell to the cytotoxic effects of radiotherapy; and
(b) administering to said subject an amount of radiotherapy sufficient to treat said cancer.

The invention also provides a method for treating a neurological disease, said method comprising administering to a subject in need thereof the compound of Formula (IX) or a pharmaceutically acceptable salt thereof, in an amount sufficient to treat said neurological disease.

For ease of reference, the compounds of Formulas (I), (Ia), (II), (III), (IV), (IVa), (V), (VI), (VII), (VIII) and (IX) will simply be referred to herein as the "Compounds of the Invention."

5.3 Preparation of the Compounds of the Invention

The Compounds of the Invention may be prepared via the synthetic procedure outlined below in Schemes 1-9. It will be apparent to one skilled in the art how to prepare the scope of the Compounds of the Invention by choice of proper and relevant starting materials, synthetic intermediates and reagents.

Accordingly, Scheme 1 illustrates a method useful for making the compounds of Formula (I).

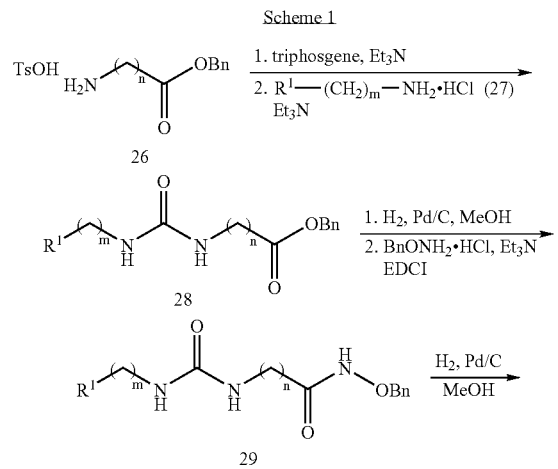

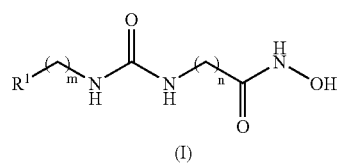

(I)

The tosylate salt of an amine of formula 26 is treated with triphosgene to provide an intermediate isocyanate which is reacted in situ with an amine of formula 27 to provide the urea of formula 28. The benzyl protecting group of compound 28 is removed using catalytic hydrogenation and the unmasked carboxylic acid is subsequently coupled with a benzyl protected hydroxylamine to provide the benzyl protected hydroxyamide of formula 29. Compound 29 is then debenzylated using catalytic hydrogenation to provide the compound of Formula (I).

Scheme 2 shows a method useful for making the compounds of Formula (II) where Y is —NHC(O)CH$_2$SH.

Scheme 2

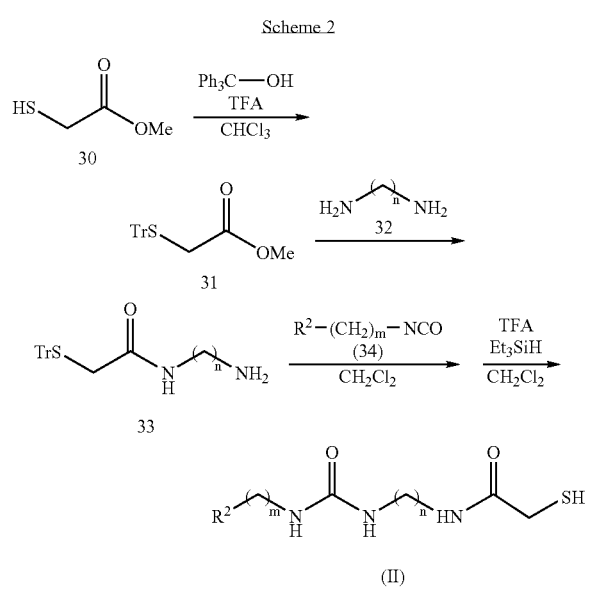

(II)

The thiol group of methylthioglycolate 30 is protected as it's trityl derivative 31, which is subsequently couples with an alkyldiamine of formula 32 to provide amine intermediate 33. Intermediate 33 is then coupled with an isocyanate of formula 34, and the trityl protecting group is removed to provide the Compound of Formula (II), where Y is —NHC(O)CH$_2$SH.

Scheme 3 shows a method useful for making the compounds of Formula (II) where Y is —C(O)CH$_2$SH.

Scheme 3

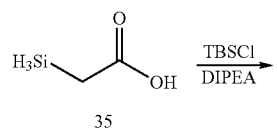

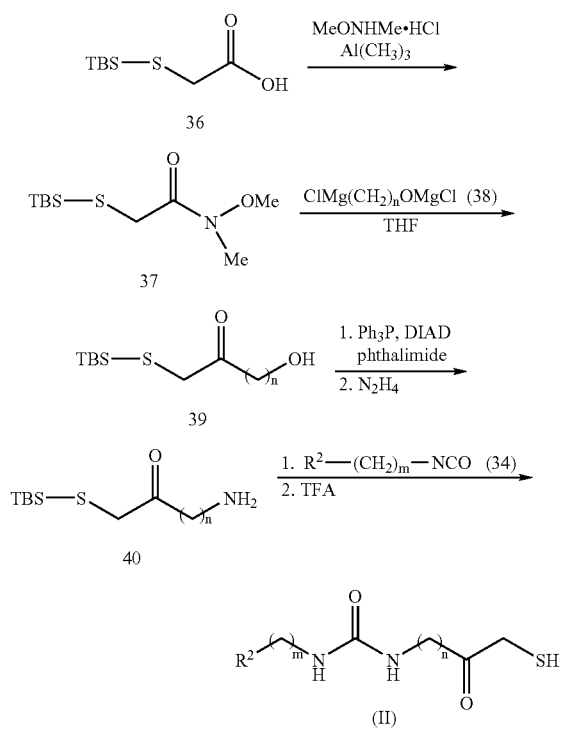

(II)

Silylated acetic acid derivative 35 is converted to TBS protected thioglycolic acid 36, which is treated with N,O-dimethylhydroxylamine hydrochloride to provide the N-methoxy-N-methyl amide 37. Compound 37 is coupled with an alkanol bis-Grignard reagent of formula 38 to provide alcohol 39, which is transformed to amine 40 using a variant of the Gabriel amine synthesis. Amine 40 is then coupled with an isocyanate of formula 34, and the coupled product is subjected to an acid-catalyzed deprotection of the silyl-protected thiol group to provide the compound of formula (II), where Y is —C(O)CH$_2$SH.

Scheme 4 depicts methodology useful for preparing the compounds of formula (III).

Scheme 4

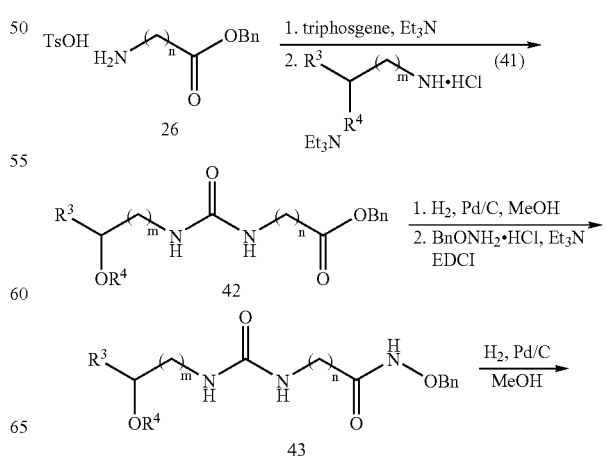

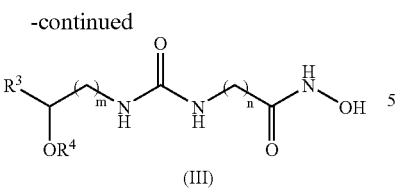

The tosylate salt of an amine of formula 26 is treated with triphosgene to provide an intermediate isocyanate which is reacted in situ with an amine of formula 41 to provide the urea of formula 42. The benzyl protecting group of compound 42 is removed using catalytic hydrogenation and the unmasked carboxylic acid is subsequently coupled with a benzyl protected hydroxylamine to provide the benzyl protected hydroxyamide of formula 43. Compound 43 is subsequently debenzylated using catalytic hydrogenation to provide the compound of Formula (III).

Scheme 5 shows a method useful for making the compounds of Formula (IV).

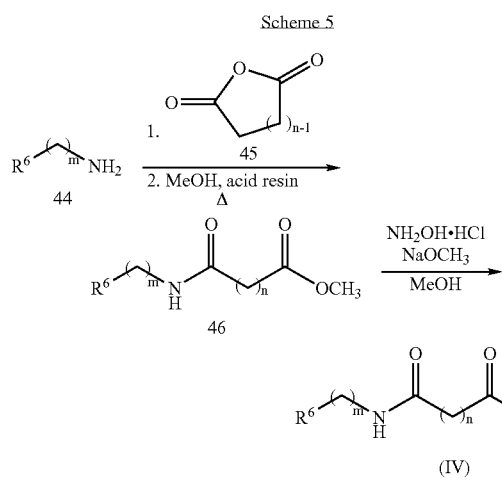

An amine of general formula 44 is subjected to an acid-catalyzed coupling with a cyclic anhydride of formula 45 in alcoholic solvent to provide ester intermediate 46, which is then converted to the hydroxyamide of Formula (IV) via treatment with hydroxylamine hydrochloride in the presence of base.

Scheme 6 illustrates methodology useful for preparing the compounds of formula (V) where Y is —NHC(O)CH$_2$SH.

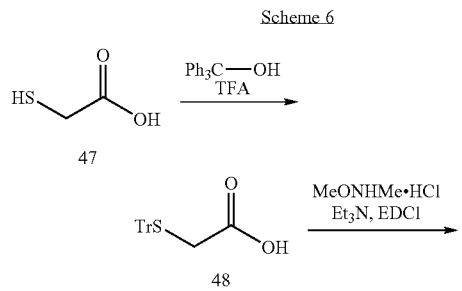

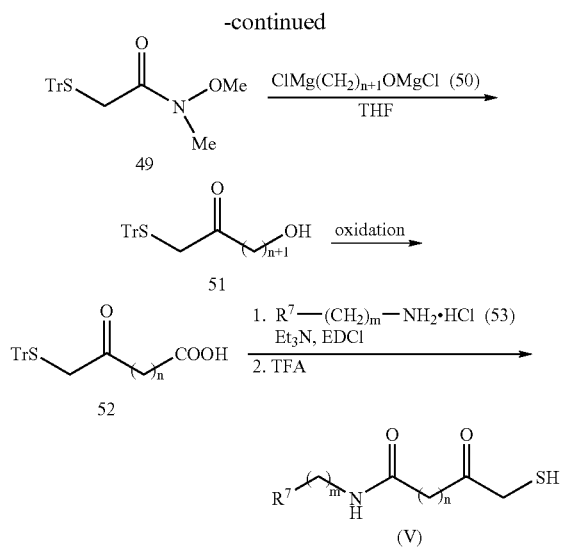

The thiol group of thioglycolic acid 47 is protected as it's trityl derivative 48, which is subsequently treated with N,O-dimethylhydroxylamine hydrochloride to provide the N-methoxy-N-methyl amide 49. Compound 49 is coupled with an alkanol bis-Grignard reagent of formula 50 to provide alcohol 51, which is oxidized to provide carboxylic acid 52. Compound 52 is coupled with an amine of formula 53 using EDCI and the thiol protecting group is removed using TFA to proivde the compound of Formula (V) where Y is —NHC(O)CH$_2$SH.

Scheme 7 illustrates methodology useful for preparing the compounds of formula (V) where Y is —C(O)CH$_2$SH.

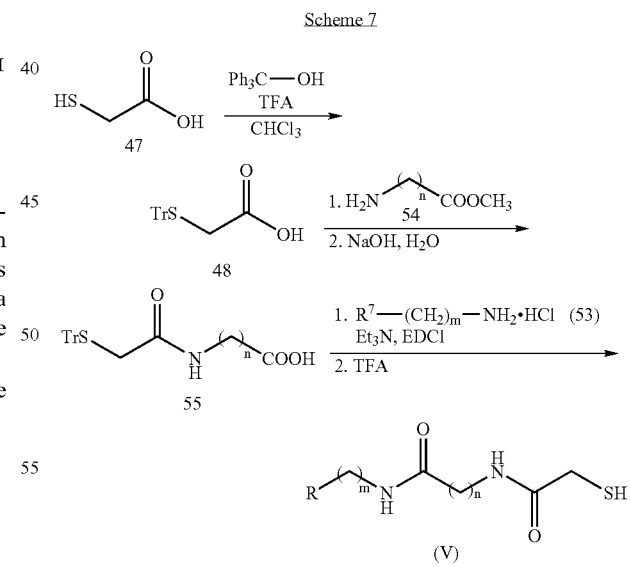

The thiol group of thioglycolic acid 47 is protected as it's trityl derivative 48, which is subsequently coupled with an alkylamine of formula 54, followed by basic hydrolysis to yield the carboxylic acid intermediate of formula 55. Intermediate 55 is then coupled with an alkylamine of formula 53, followed by removal of the trityl group to provide the Compound of Formula (V), where Y is —NHC(O)CH$_2$SH.

Scheme 8 shows a method useful for preparing the compounds of formulas (VI) and (VII) wherein the integers m and n are the same.

Alternatively, Scheme 9 illustrates how Scheme 8 can be modified to provide compound of Formulas (VI) and (VII) having different values of m and n by reacting compound 56

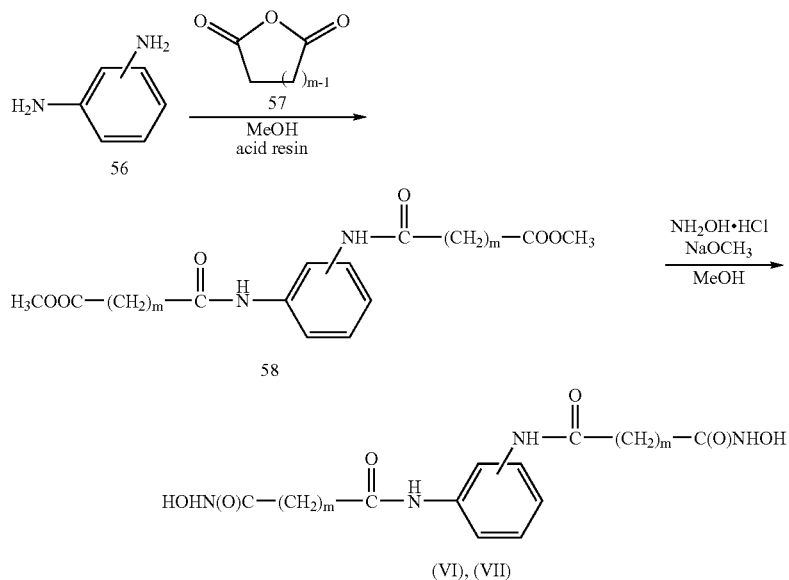

A phenyldiamine of general formula 56 is coupled with an excess of a cyclic anhydride of formula 57 to provide a diester intermediate of formula 58, which is subsequently converted to the dihydroxyamides of Formulas (VI) and (VII) upon treatment with hydroxylamine hydrochloride.

with one equivalent of the cyclic anhydride of formula 57 and reacting the product of this reaction with one equivalent of the cyclic anhydride of formula 59 to provide the diester intermediate of formula 60, which can be brought forward to the compounds of formula (VI) and (VII) using the methodology shown in Scheme 8.

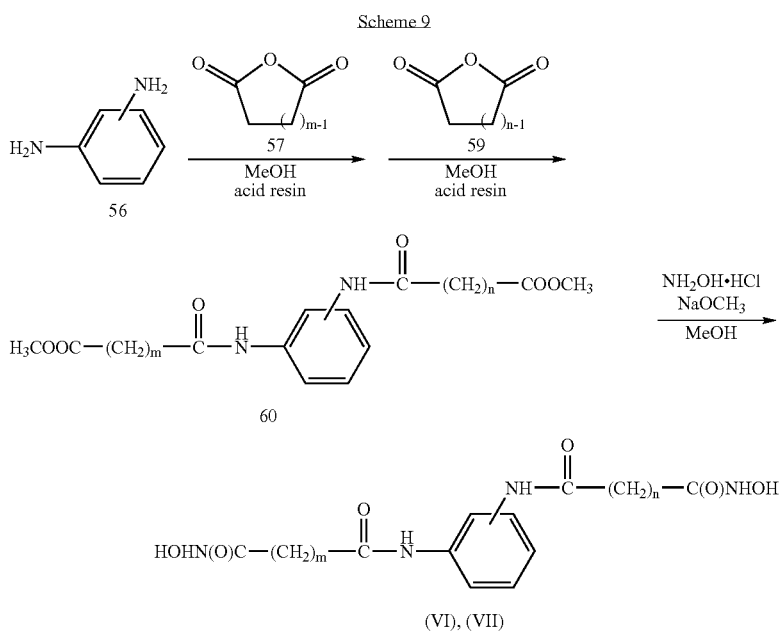

It will be apparent to a person of ordinary skill in the art of organic synthesis how to prepare the componds of formulas (VI) and (VII) having Z groups which are not identical by sequentially subjecting diamine 56 to the any two of the chemical methodologies described in schemes 6, 7 or 8 in proper stoiciometric amounts.

Scheme 10 illustrates methodology useful for preparing the compounds of formula (VIII).

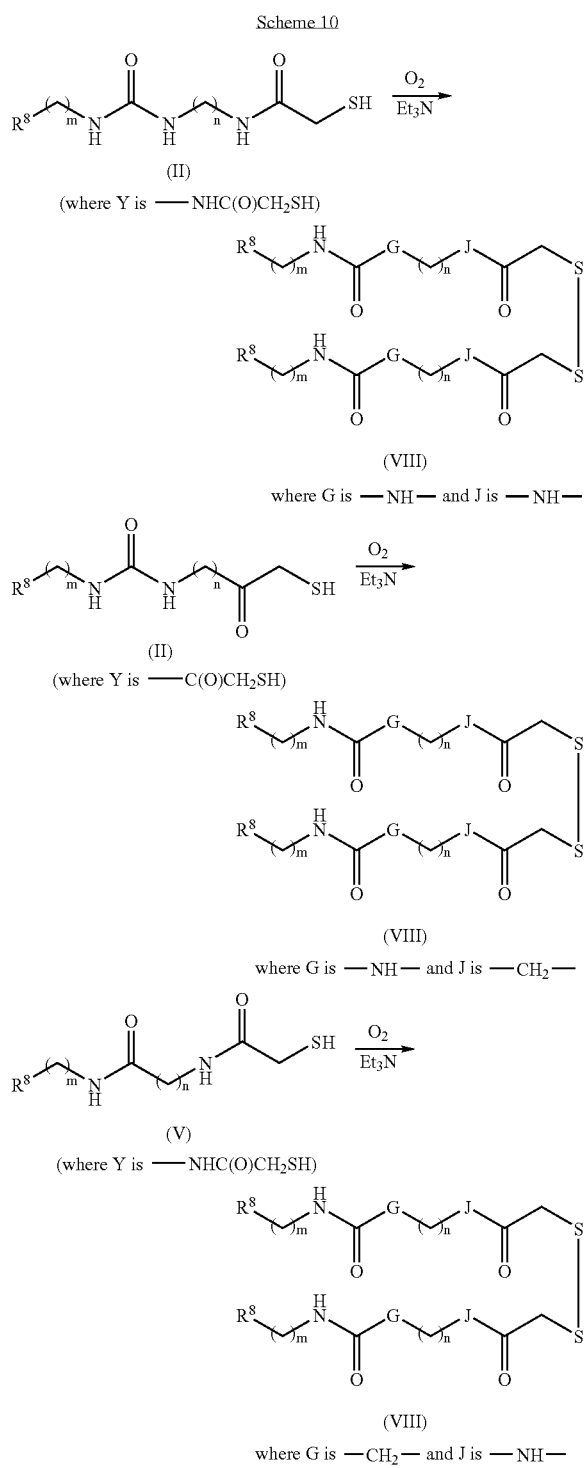

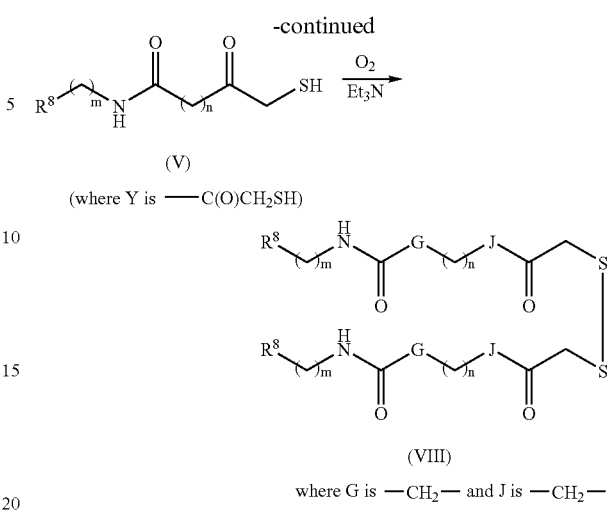

The thiol groups of Compounds of Formulas (II) and (V) may be oxidatively self-coupled in the presence of triethylamine to provide the disulfide compounds of Formula (VIII).

It will be apparant to a person of ordinary skill in the art of organic synthesis how to prepare the componds of formulas (VIII) and non-identical $R^8$ and/or G and/or J and/or m and/or n groups by using the methodology described in Scheme 10 to heterocouple two non-identical compounds of formula (II), two non-identical compounds of formula (V) or a compound of formula (II) and a compound of formula (V).

5.6 Pharmaceutical Compositions and Therapeutic Administration

In other aspects, the present invention provides a pharmaceutical composition comprising an effective amount of a Compound of the Invention and a pharmaceutically acceptable carrier or vehicle. The pharmaceutical compositions are suitable for veterinary or human administration.

The pharmaceutical compositions of the present invention can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc., and is more preferably a mammal, and most preferably a human.

The compositions of the invention can be in the form of a solid, liquid or gas (aerosol). Typical routes of administration may include, without limitation, oral, topical, parenteral, sublingual, rectal, vaginal, ocular, and intranasal. Parenteral administration includes subcutaneous injections, intravenous, intramuscular, intraperitoneal, intrapleural, intrastemal injection or infusion techniques. Preferably, the compositions are administered parenterally, most preferably intravenously. Pharmaceutical compositions of the invention can be formulated so as to allow a Compound of the Invention to be bioavailable upon administration of the composition to a subject. Compositions can take the form of one or more dosage units, where for example, a tablet can be a single dosage unit, and a container of a Compound of the Invention in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of cancer the subject is in need of treatment of, the use of the composition as part of a multi-drug regimen, the particular form of the Compound of the Invention, the manner of administration, and the composition employed.

The pharmaceutically acceptable carrier or vehicle may be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, e.g., inhalatory administration.

The composition may be intended for oral administration, and if so, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as ethyl cellulose, carboxymethylcellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the pharmaceutical composition is in the form of a capsule, e.g., a gelatin capsule, it can contain, in addition to materials of the above type, a liquid carrier such as polyethylene glycol, cyclodextrin or a fatty oil.

The pharmaceutical composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or diglycerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in ampoule, a disposable syringe or a multiple-dose vial made of glass, plastic or other material. Physiological saline is a preferred adjuvant. An injectable composition is preferably sterile.

The amount of the Compound of the Invention that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The pharmaceutical compositions comprise an effective amount of a Compound of the Invention such that a suitable dosage will be obtained. Typically, this amount is at least 0.01% of a Compound of the Invention by weight of the composition. When intended for oral administration, this amount can be varied to be between 0.1% and 80% by weight of the composition. Preferred oral compositions can comprise from between 4% and 50% of the Compound of the Invention by weight of the composition. Preferred compositions of the present invention are prepared so that a parenteral dosage unit contains from between 0.01% and 2% by weight of the Compound of the Invention.

Generally, the dosage of a Compound of the Invention administered to a subject is typically between 0.1 mg/kg and 100 mg/kg of the subject's body weight. In one embodiment, the dosage administered to a subject is between 0.5 mg/kg and 50 mg/kg of the subject's body weight, more preferably between 1 mg/kg and 25 mg/kg of the subject's body weight.

In a specific embodiment, when the Compounds of the Invention are used in combination with radiotherapy, a Compound of the Invention can be administered in amounts that result in concentrations in the fluid of a target tissue that are less than about twice the $IC_{50}$ concentration for the particular compound, more preferably about equal to the $IC_{50}$ concentration. The $IC_{50}$ concentration is defined as the concentration of the Compound of the Invention that kills 50% of cells following treatment with the Compound of the Invention.

In another embodiment, the Compounds of the Invention may be administered at amounts lower than the $IC_{50}$ concentration, such as about 50% of the $IC_{50}$ concentration, about 40% of the $IC_{50}$ concentration, about 30% of the $IC_{50}$ concentration, about 20% of the $IC_{50}$ concentration, about 10% or about 5% of the $IC_{50}$ concentration, at the target tissue.

In still another embodiment, the Compounds of the Invention may be administered locally so that the concentration at the target tissue is in the effective range and the concentration in non-target tissue is minimized.

In another embodiment, the dosage of the Compound of the Invention results in a concentration at a target tissue that does not promote apoptosis of cells in culture yet is effective in increasing cell death in neoplastic cells exposed to radiation or recognized chemotherapeutic chemical agents. Concentrations that produce these effects can be determined for a Compound of the Invention by one of skill in the art using markers of apoptosis, including, but not limited to, the apoptotic index and caspase activities.

The Compounds of the Invention can be administered by any convenient route, for example by infusion or bolus injection, by absorption through epithelial or mucocutaneous linings (e.g., oral mucosa, rectal and intestinal mucosa, etc.). Administration can be systemic or local. Various delivery systems are known, e.g., microparticles, microcapsules, capsules, etc., and may be useful for administering a Compound of the Invention. In certain embodiments, more than one Compound of the Invention is administered to a subject. Methods of administration may include, but are not limited to, oral administration and parenteral administration; parenteral administration including, but not limited to, intradermal, intramuscular, intraperitoneal, intravenous, subcutaneous; intranasal, epidural, sublingual, intranasal, intracerebral, intraventricular, intrathecal, intravaginal, transdermal, rectally, by inhalation, or topically to the ears, nose, eyes, or skin.

The preferred mode of administration is left to the discretion of the practitioner, and will depend in-part upon the site of the medical condition (such as the site of cancer, a cancerous tumor or a pre-cancerous condition).

In one embodiment, the Compounds of the Invention are administered orally.

In another embodiment, the Compounds of the Invention are administered parenterally.

In still another embodiment, the Compounds of the Invention are administered intravenously.

In specific embodiments, it can be desirable to administer one or more Compounds of the Invention locally to the area in need of treatment. This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as sialastic membranes, or fibers. In one embodiment, administration can be by direct injection at the site (or former site) of a cancer, tumor, or precancerous tissue. In certain embodiments, it can be desirable to introduce one or more Compounds of the Invention into the central nervous system by any suitable route, including intraventricular and intrathecal injection. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Compounds of the Invention can be formulated as a suppository, with traditional binders and carriers such as triglycerides.

In one embodiment, the Compounds of the Invention can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the Compounds of the Invention can be delivered in a controlled release system. In one embodiment, a pump can be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled-release system can be placed in proximity of the target of the Compounds of the Invention, e.g., the brain, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The term "carrier" refers to a diluent, adjuvant or excipient, with which a Compound of the Invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a subject, the Compounds of the Invention and pharmaceutically acceptable carriers are sterile. Water is a preferred carrier when the Compound of the Invention is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable carrier is a capsule (see e.g., U.S. Pat. No. 5,698,155). Other examples of suitable pharmaceutical carriers are described in "Remington's Pharmaceutical Sciences" by E. W. Martin.

Sustained or directed release compositions that may be formulated include, but are not limited to liposomes or other formulations wherein the active component is protected with differentially degradable coatings, e.g., by microencapsulation, multiple coatings, etc. It is also possible to freeze-dry the new compositions and use the lyophilizates obtained, for example, for the preparation of products for injection.

In a preferred embodiment, the Compounds of the Invention are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a Compound of the Invention is to be administered by infusion, it can be dispensed, for example, with an infusion bottle containing sterile pharmaceutical grade water or saline. Where the Compound of the Invention is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving complex are also suitable for orally administered compositions of the invention. In these later platforms, fluid from the environment surrounding the capsule is imbibed by the driving complex, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard carriers such as mannitol, lactose, starch, magnesium stearate, sodium saccharine, cellulose, magnesium carbonate, etc. Such carriers are preferably of pharmaceutical grade.

The pharmaceutical compositions of the invention can be intended for topical administration, in which case the carrier can be in the form of a solution, emulsion, ointment or gel base. The base, for example, can comprise one or more of the following: petrolatum, lanolin, polyethylene glycols, beeswax, mineral oil, diluents such as water and alcohol, and emulsifiers and stabilizers. Thickening agents can be present in a composition for topical administration. If intended for transdermal administration, the composition can be in the form of a transdermal patch or an iontophoresis device. Topical formulations can comprise a concentration of a Compound of the Invention of from between 0.01% and 10% w/v (weight per unit volume of composition).

The compositions can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

The compositions can consist of gaseous dosage units, e.g., it can be in the form of an aerosol. The term aerosol is used to denote a variety of systems ranging from those of colloidal nature to systems consisting of pressurized packages. Delivery can be by a liquefied or compressed gas or by a suitable pump system that dispenses the active ingredients. Aerosols of the compositions can be delivered in single phase, bi-phasic, or tri-phasic systems in order to deliver the composition. Delivery of the aerosol includes the necessary container, activators, valves, subcontainers, Spacers and the like, which together can form a kit. Preferred aerosols can be determined by one skilled in the art, without undue experimentation.

Whether in solid, liquid or gaseous form, the compositions of the present invention can comprise an additional therapeutically active agent selected from among those including, but not limited to, an additional anticancer agent, an antiemetic agent, a hematopoietic colony stimulating factor, an antidepressant and an analgesic agent.

The pharmaceutical compositions can be prepared using methodology well known in the pharmaceutical art. For example, a composition intended to be administered by injection can be prepared by combining a Compound of the Invention with water so as to form a solution. A surfactant can be added to facilitate the formation of a homogeneous solution or suspension. Surfactants are complexes that can non-covalently interact with a Compound of the Invention so as to facilitate dissolution or homogeneous suspension of the Compound of the Invention in the aqueous delivery system.

In one embodiment, the pharmaceutical compositions of the present invention may comprise one or more additional anticancer agents.

In another embodiment, the pharmaceutical compositions of the present invention can be administered prior to, at the same time as, or after an additional anticancer agent, or on the same day, or within 1 hour, 2 hours, 12 hours, 24 hours, 48 hours, 72 hours, 1 week, 2 weeks, 3 weeks or 4 weeks of each other.

In one embodiment, the pharmaceutical compositions of the present invention may comprise one or more known therapeutically active agents.

In another embodiment, the pharmaceutical compositions of the present invention can be administered prior to, at the same time as, or after an antiemetic agent, or on the same day, or within 1 hour, 2 hours, 12 hours, 24 hours, 48 hours or 72 hours of each other.

In another embodiment, the pharmaceutical compositions of the present invention can be administered prior to, at the same time as, or after a hematopoietic colony stimulating factor, or on the same day, or within 1 hour, 2 hours, 12 hours, 24 hours, 48 hours, 72 hours, 1 week, 2 weeks, 3 weeks or 4 weeks of each other.

In another embodiment, the pharmaceutical compositions of the present invention can be administered prior to, at the same time as, or after an opioid or non-opioid analgesic agent, or on the same day, or within 1 hour, 2 hours, 12 hours, 24 hours, 48 hours or 72 hours of each other.

In another embodiment, the pharmaceutical compositions of the present invention can be administered prior to, at the same time as, or after an anti-depressant agent, or on the same day, or within 1 hour, 2 hours, 12 hours, 24 hours, 48 hours or 72 hours of each other.

5.7 Kits

The invention encompasses kits that can simplify the administration of the Compounds of the Invention or composition of the invention to a subject.

A typical kit of the invention comprises unit dosages of the Compounds of the Invention. In one embodiment, the unit dosage form is in a container, which can be sterile, containing an effective amount of one of the Compounds of the Invention and a pharmaceutically acceptable carrier or vehicle. In another embodiment, the unit dosage form is in a container containing an effective amount of one of the Compounds of the Invention as a lyophilate. In this instance, the kit can further comprise another container which contains a solution useful for the reconstitution of the lyophilate. The kit can also comprise a label or printed instructions for use of the Compounds of the Invention. In one embodiment, the kit comprises multiple containers: (a) a first container containing an unit dosage form of Compound of the Invention, and (b) one or more additional containers each containing a unit dosage form of one or more additional anticancer agents or pharmaceutically acceptable salts thereof. In another embodiment the kit comprises a container containing a therapeutically active agent such as an antiemetic agent, a hematopoietic colony-stimulating factor, an analgesic agent or an anxiolytic agent.

In a further embodiment, the kit comprises a unit dosage form of a pharmaceutical composition of the invention.

Kits of the invention can further comprise one or more devices that are useful for administering the unit dosage forms of the Compounds of the Invention or a pharmaceutical composition of the invention. Examples of such devices include, but are not limited to, a syringe, a drip bag, a patch or an enema, which optionally contain the unit dosage forms.

5.8 Therapeutic Uses

The Compounds of the Invention are useful for treating cancer and neurological diseases. The Compounds of the Invention are also useful for increasing the sensitivity of a cancer cell to the cytotoxic effects of radiotherapy.

5.8.1 Treatment of Cancer

Cancer can be treated or prevented by administration of amounts of the Compounds of the invention that are effective to treat cancer or by administration of a pharmaceutical composition comprising amounts of the Compounds of the invention that are effective to treat cancer.

5.8.1.1 Therapeutic Methods

In a preferred embodiment, the present invention provides methods for treating cancer, including but not limited to: killing a cancer cell or neoplastic cell; inhibiting the growth of a cancer cell or neoplastic cell; inhibiting the replication of a cancer cell or neoplastic cell; or ameliorating a symptom thereof, said methods comprising administering to a subject in need thereof an amount of the Compounds of the invention effective to treat cancer.

In one embodiment, the invention provides a method for treating cancer, said method comprising administering to a subject in need thereof an amount of a Compound of the Invention or a pharmaceutically acceptable salt thereof, said amount sufficient to treat said cancer.

In another embodiment, the invention provides a method for increasing the sensitivity of a cancer cell to the cytotoxic effects of radiotherapy, said method comprising contacting said cell with a Compound of the Invention or a pharmaceutically acceptable salt thereof, in an amount sufficient to increase the sensitivity of said cell to the cytotoxic effects of radiotherapy.

In a further embodiment, the present invention provides a method for treating cancer, said method comprising: (a) administering to a subject in need thereof an amount of a Compound of the Invention; and (b) administering to said subject an amount of radiotherapy. In one emodiment, the amounts administered are each effective to treat cancer. In another specific embodiment, the amounts are together effective to treat cancer. The Compound of the Invention and radiotherapy can act additively or synergistically.

In another embodiment, the invention provides a method for treating cancer, said method comprising administering to a subject in need thereof a pharmaceutical composition comprising an amount of a Compound of the Invention effective to treat cancer.

The combination therapy of the invention can be used accordingly in a variety of settings for the treatment of various cancers.

In a specific embodiment, the subject in need of treatment has previously undergone treatment for cancer. Such previous treatments include, but are not limited to, prior chemotherapy, radiotherapy, surgery, or immunotherapy, such as cancer vaccines.

In another embodiment, the cancer being treated is a cancer which has demonstrated sensitivity to radiotherapy or is known to be responsive to radiotherapy. Such cancers include, but are not limited to, Non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophogeal cancer, rectal cancer, small-cell lung cancer, non-small cell lung cancer, brain tumors, or other CNS neoplasms.

In still another embodiment, the cancer being treated is a cancer which has demonstrated resistance to radiotherapy or is known to be refractory to radiotherapy. A cancer may be determined to be refractory to a therapy when at least some significant portion of the cancer cells are not killed or their cell division are not arrested in response to therapy. Such a determination can be made either in vivo or in vitro by any method known in the art for assaying the effectiveness of treatment on cancer cells, using the art-accepted meanings of "refractory" in such a context. In a specific embodiment, a cancer is refractory where the number of cancer cells has not been significantly reduced, or has increased.

Other cancers that can be treated with the Compounds and methods of the Invention include, but are not limited to, cancers disclosed below in Table 1 and metastases thereof.

TABLE 1

Solid tumors, including but not limited to:
fibrosarcoma
myxosarcoma
liposarcoma
chondrosarcoma
osteogenic sarcoma
chordoma
angiosarcoma
endotheliosarcoma
lymphangiosarcoma
lymphangioendotheliosarcoma
synovioma
mesothelioma
Ewing's tumor
leiomyosarcoma
rhabdomyosarcoma
colon cancer
colorectal cancer
kidney cancer
pancreatic cancer
bone cancer
breast cancer
ovarian cancer
prostate cancer
esophageal cancer
stomach cancer
oral cancer
nasal cancer
throat cancer
squamous cell carcinoma
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
testicular cancer
small cell lung carcinoma
bladder carcinoma
lung cancer
epithelial carcinoma
glioma
glioblastoma multiforme
astrocytoma
medulloblastoma
craniopharyngioma
ependymoma
pinealoma
hemangioblastoma
acoustic neuroma
oligodendroglioma
meningioma
skin cancer
melanoma TABLE 1-continued neuroblastoma
    retinoblastoma
    blood-borne cancers, including but not limited to:
        acute lymphoblastic leukemia ("ALL")
        acute lymphoblastic B-cell leukemia
        acute lymphoblastic T-cell leukemia
        acute myeloblastic leukemia ("AML")
        acute promyelocytic leukemia ("APL")
        acute monoblastic leukemia
        acute erythroleukemic leukemia
        acute megakaryoblastic leukemia
        acute myelomonocytic leukemia
        acute nonlymphocytic leukemia
        acute undifferentiated leukemia
        chronic myelocytic leukemia ("CML")
        chronic lymphocytic leukemia ("CLL")
        hairy cell leukemia
        multiple myeloma
    acute and chronic leukemias:
        lymphoblastic
        myelogenous
        lymphocytic
        myelocytic leukemias
    Lymphomas:
        Hodgkin's disease
        non-Hodgkin's Lymphoma
        Multiple myeloma
        Waldenstrom's macroglobulinemia
        Heavy chain disease
        Polycythemia vera In one embodiment, the cancer is selected from the group consisting of Non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophageal cancer, rectal cancer, small-cell lung cancer, non-small cell lung cancer, brain tumors, and other CNS neoplasms.

5.8.1.2 Prophylactic Methods

The Compounds of the Invention can also be administered to prevent progression to a neoplastic or malignant state, including but not limited to the cancers listed in Table 1. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68-79). Hyperplasia is a form of controlled cell proliferation involving an increase in cell number in a tissue or organ, without significant alteration in structure or function. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a subject, can indicate the desirability of prophylactic/therapeutic administration of the composition of the invention. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

The prophylactic use of the compounds and methods of the present invention are also indicated in some viral infections that may lead to cancer. For example, human papilloma virus can lead to cervical cancer (see, e.g., Hemandez-Avila et al., Archives of Medical Research (1997) 28:265-271), Epstein-Barr virus (EBV) can lead to lymphoma (see, e.g., Herrmann et al., J Pathol (2003) 199(2):140-5), hepatitis B or C virus can lead to liver carcinoma (see, e.g., El-Serag, J Clin Gastroenterol (2002) 35(5 Suppl 2):S72-8), human T cell leukemia virus (HTLV)-I can lead to T-cell leukemia (see e.g., Mortreux et al., Leukemia (2003) 17(1):26-38), human herpesvirus-8 infection can lead to Kaposi's sarcoma (see, e.g., Kadow et al., Curr Opin Investig Drugs (2002) 3(11):1574-9), and Human Immune deficiency Virus (HIV) infection contribute to cancer development as a consequence of immunodeficiency (see, e.g., Dal Maso et al., Lancet Oncol (2003) 4(2):110-9).

In other embodiments, a subject which exhibits one or more of the following predisposing factors for malignancy can treated by administration of the compounds or methods of the invention: a chromosomal translocation associated with a malignancy (e.g., the Philadelphia chromosome for chronic myelogenous leukemia, t(14; 18) for follicular lymphoma, etc.), familial polyposis or Gardner's syndrome (possible forerunners of colon cancer), benign monoclonal gammopathy (a possible forerunner of multiple myeloma), a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W. B. Saunders Co., Philadelphia, pp. 112-113) etc.), and exposure to carcinogens (e.g., smoking, and inhalation of or contacting with certain chemicals).

In another specific embodiment, the compounds and methods of the invention are administered to a human subject to prevent progression to breast, colon, ovarian, or cervical cancer.

5.8.1.3 Multi-Modality Therapy for Cancer

The Compounds of the Invention can be administered to a subject that has undergone or is currently undergoing one or more additional anticancer treatment modalities including, but not limited to, chemotherapy, radiotherapy, surgery or immunotherapy, such as cancer vaccines.

In one embodiment, the invention provides methods for treating cancer comprising (a) administering to a subject in need thereof an amount of a combination therapy of the invention; and (b) administering to said subject one or more additional anticancer treatment modalities including, but not limited to, radiotherapy, chemotherapy, surgery or immunotherapy, such as a cancer vaccine. In one embodiment, the administering of step (a) is done prior to the administering of step (b). In another embodiement, the administering of step (a) is done subsequent to the administering of step (b). In still another embodiment, the administering of step (a) is done concurrently with the administering of step (b).

In one embodiment, the additional anticancer treatment modality is chemotherapy.

In another embodiment, the additional anticancer treatment modality is surgery.

In still another embodiment, the additional anticancer treatment modality is immunotherapy, such as cancer vaccines.

In one embodiment, the Compound of the Invention or a pharmaceutically acceptable salt thereof is administered adjunctively with the additional anticancer treatment modality.

In another embodiment, the Compound of the Invention or a pharmaceutically acceptable salt thereof acts synergistically with radiotherapy.

In a preferred embodiment, the additional anticancer treatment modality is radiotherapy. In the methods of the present invention, any radiotherapy protocol can be used depending upon the type of cancer to be treated. For example, but not by way of limitation, X-ray radiation can be administered; in particular, high-energy megavoltage (radiation of greater that 1 MeV energy) can be used for deep tumors, and electron beam and orthovoltage X-ray radiation can be used for skin cancers. Gamma-ray emitting radioisotopes, such as radioactive isotopes of radium, cobalt and other elements, can also be administered. Illustrative radiotherapy protocols useful in the present invention include, but are not limited to, stereotactic methods where multiple sources of low dose radiation are simultaneously focused into a tissue volume from multiple angles; "internal radiotherapy," such as brachytherapy, interstitial irradiation, and intracavitary irradiation, which involves the placement of radioactive implants directly in a tumor or other target tissue; intraoperative irradiation, in which a large dose of external radiation is directed at the target tissue which is exposed during surgery; and particle beam radiotherapy, which involves the use of fast-moving subatomic particles to treat localized cancers.

In a preferred embodiment, the Compound of the Invention or a pharmaceutically acceptable salt thereof is administered prior to the administration of radiotherapy.

In another preferred embodiment, the Compound of the Invention or a pharmaceutically acceptable salt thereof is administered adjunctively with radiotherapy.

The Compound of the Invention and the additional treament modalities of the combination therapies of the invention can act additively or synergistically (i.e., the combination of an Compound of the Invention or a pharmaceutically acceptable salt thereof, and an additional anticancer treatment modality is more effective than their additive effects when each are administered alone). A synergistic combination permits the use of lower dosages of the Compound of the Invention and/or the additional treatment modality and/or less frequent administration of the Compound of the Invention and/or additional treatment modality to a subject with cancer. The ability to utilize lower dosages of a Compound of the Invention and/or an additional treatment modality and/or to administer a Compound of the Invention and said additional treatment modality less frequently can reduce the toxicity associated with the administration of a Compound of the Invention and/or the additional treatement modality to a subject without reducing the efficacy of a Compound of the Invention and/or the additional treatement modality in the treatment of cancer. In addition, a synergistic effect can result in the improved efficacy of the treatment of cancer and/or the reduction of adverse or unwanted side effects associated with the administration of a Compound of the Invention and/or an additional anticancer treatment modality as monotherapy.

In one embodiment, the Compounds of the Invention may act synergistically with radiotherapy when administered in doses typically employed when such agents are used alone for the treatment of cancer. In another embodiment, the Compounds of the Invention may act synergistically with radiotherapy when administered in doses that are less than doses typically employed when such agents are used as monotherapy for the treatment of cancer.

In one embodiment, radiotherapy may act synergistically with a Compound of the Invention when administered in doses typically employed when radiotherapy is used as monotherapy for the treatment of cancer. In another embodiment, radiotherapy may act synergistically with a Compound of the Invention when administered in doses that are less than doses typically employed when radiotherapy is used as monotherapy for the treatment of cancer.

In a specific embodiment, the Compounds of the Invention act as HDAC inhibitors.

The effectiveness of the use of the Compounds of the Invention as HDAC inhibitors for sensitizing cancer cells to the effect of radiotherapy can be determined by the in vitro and/or in vivo determination of post-treatment survival using techniques known in the art. In one embodiment, for in vitro determinations, exponentially growing cells can be exposed to known doses of radiation and the survival of the cells monitored. Irradiated cells are plated and cultured for about 14- about 21 days, and the colonies are stained. The surviving fraction is the number of colonies divided by the plating efficiency of unirradiated cells. Graphing the surviving fraction on a log scale versus the absorbed dose on a linear scale generates a survival curve. Survival curves generally show an exponential decrease in the fraction of surviving cells at higher radiation doses after an initial shoulder region in which the dose is sublethal. A similar protocol can be used for chemical agents when used in the combination therapies of the invention.

Inherent radiosensitivity of tumor cells and environmental influences, such as hypoxia and host immunity, can be further assessed by in vivo studies. The growth delay assay is commonly used. This assay measures the time interval required for a tumor exposed to radiation to regrow to a specified volume. The dose required to control about 50% of tumors is determined by the $TCD_{50}$ assay.

In vivo assay systems typically use transplantable solid tumor systems in experimental subjects. Radiation survival parameters for normal tissues as well as for tumors can be assayed using in vivo methods known in the art.

Two mathematical models are commonly employed to analyze radiation survival data. A first model is the multi-target model. In this analysis, the reciprocal of the slope of the survival curve is defined as Do, the radiosensitivity of the cell population or tissue under investigation. Do is the dose required to reduce the surviving fraction to about 37% in the exponential portion of the survival curve. The extrapolation of the linear portion of the curve to the y-intercept is denoted n. The width of the shoulder region is represented by drawing a line from the 100% survival point to the extrapolation line, this width is denoted Dq. Dq is the quasi-threshold dose, or the point at which the reduction in surviving fraction as a function of radiation dosage becomes exponential. The Dq value can also provide an estimate of an additional total dose required for each division of a single dose therapy into fractional doses. The additional dose is required to overcome the effect of sublethal damage repair that occurs when two sublethal doses are separated in time.

The linear quadratic model (surviving fraction=$e^{\alpha u - RD2}$) is used to fit radiation survival data to a continuously bending curve, where D is dose and a and (3 are constants. Alpha is the linear component, a measure of the initial slope that represents single-hit killing kinetics and dominates the radiation response at low doses. Beta is the quadratic component of cell killing, that represents multiple-hit killing and causes the curve to bend at higher doses. The alpha:beta ratio is the dose at which the linear and quadratic components of cell killing are equal. The more linear the response to killing of cells at low radiation dose, the higher is the value of alpha, and the greater is the radiosensitivity of the cells.

When the Compound of the Invention and additional anticancer treatment modality are administered to a subject concurrently, the term "concurrently" is not limited to the administration of a Compound of the Invention and an additional anticancer treatment modality at exactly the same time, but rather it is meant that they are administered to a subject in a sequence and within a time interval such that they can act synergistically to provide an increased benefit than if they were administered otherwise. For example, the Compounds of the Invention may be administered at the same time or sequentially in any order at different points in time as an additional anticancer treament modality; however, if not administered at the same time, they should be administered sufficiently close in time so as to provide the desired therapeutic effect, preferably in a synergistic fashion. The Compound of the Invention and the additional anticancer treatment modality can be administered separately, in any appropriate form and by any suitable route. When the Compound of the Invention and the additional anticancer treatment modality are not administered concurrently, it is understood that they can be administered in any order to a subject in need thereof. For example, a Compound of the Invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional anticancer treatment modality (e.g., radiotherapy), to a subject in need thereof. In various embodiments the Compound of the Invention and the additional anticancer treatment modality are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies of the invention are administered within the same office or hospital visit. In another embodiment, the Compound of the Invention and the additional anticancer treatment modality are administered at 1 minute to 24 hours apart.

In one embodiment, a Compound of the Invention is administered prior or subsequent to an additional anticancer treatment modality, preferably at least an hour, five hours, 12 hours, a day, a week, a month, more preferably several months (e.g., up to three months), prior or subsequent to administration of an additional anticancer treatment modality.

The present invention provides methods of treating cancers comprising the administration of an effective amount of a Compound of the Invention in conjunction with recognized methods of surgery, radiotherapy and chemotherapies, including, for example, chemical-based mimics of radiotherapy whereby a synergistic enhancement of the effectiveness of the recognized therapy is achieved. The effectiveness of a treatment may be measured in clinical studies or in model systems, such as a tumor model in mice, or cell culture sensitivity assays.

The present invention provides combination therapies that result in improved effectiveness and/or reduced toxicity. Accordingly, in one aspect, the invention relates to the use of the Compounds of the Invention as radiosensitizers in conjunction with radiotherapy.

When the combination theapy of the invention comprises administering a Compound of the Invention are with one or more additional anticancer agents, the Compound of the Invention and the additional anticancer agents can be administered concurrently or sequentially to a subject. The agents can also be cyclically administered. Cycling therapy involves the administration of one or more anticancer agents for a period of time, followed by the administration of one or more different anticancer agents for a period of time and repeating this sequential administration, i.e., the cycle, in order to reduce the development of resistance to one or more of the anticancer agents of being administered, to avoid or reduce the side effects of one or more of the anticancer agents being administered, and/or to improve the efficacy of the treatment.

An additional anticancer agent may be administered over a series of sessions; any one or a combination of the additional anticancer agents listed below may be administered.

The present invention includes methods for treating cancer, comprising administering to a subject in need thereof a Compound of the Invention, and one or more additional anticancer agents or pharmaceutically acceptable salts thereof. The Compound of the Invention and the additional anticancer agent(s) can act additively or synergistically. Suitable anticancer agents include, but are not limited to, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epirubicin, 5-fluorouracil (5-FU), taxanes such as docetaxel and paclitaxel, leucovorin, levamisole, irinotecan, estramustine, etoposide, nitrogen mustards, BCNU, nitrosoureas such as cannustine and lomustine, vinca alkaloids such as vinblastine, vincristine and vinorelbine, platinum complexes such as cisplatin, carboplatin and oxaliplatin, imatinib mesylate, hexamethylmelamine, topotecan, tyrosine kinase inhibitors, tyrphostins herbimycin A, genistein, erbstatin, and lavendustin A.

In one embodiment, the anti-cancer agent can be, but is not limited to, a drug listed in Table 2.

TABLE 2

| Alkylating agents | |
|---|---|
| Nitrogen mustards: | Cyclophosphamide |
| | Ifosfamide |
| | Trofosfamide |
| | Chlorambucil |
| Nitrosoureas: | Carmustine (BCNU) |
| | Lomustine (CCNU) |
| Alkylsulphonates: | Busulfan |
| | Treosulfan |
| Triazenes: | Dacarbazine |
| Platinum complexes: | Cisplatin |
| | Carboplatin |
| | Oxaliplatin |
| Plant Alkaloids | |
| Vinca alkaloids: | Vincristine |
| | Vinblastine |
| | Vindesine |
| | Vinorelbine |
| Taxoids: | Paclitaxel |
| | Docetaxel |
| DNA Topoisomerase Inhibitors | |
| Epipodophyllins: | Etoposide |
| | Teniposide |
| | Topotecan |
| | 9-aminocamptothecin |
| | Camptothecin |
| | Crisnatol |
| Mitomycins: | Mitomycin C |
| | Anti-metabolites |
| Anti-folates: | |
| DHFR inhibitors: | Methotrexate |
| | Trimetrexate |
| IMP dehydrogenase Inhibitors: | Mycophenolic acid |
| | Tiazofurin |
| | Ribavirin |
| | EICAR |
| Ribonucleotide reductase Inhibitors: | Hydroxyurea |
| | Deferoxamine |
| Pyrimidine analogs: | |
| Uracil analogs: | 5-Fluorouracil |
| | Floxuridine |
| | Doxifluridine |
| | Ratitrexed |
| Cytosine analogs: | Cytarabine (ara C) |
| | Cytosine arabinoside |
| | Fludarabine |
| | Gemcitabine |
| | Capecitabine |
| Purine analogs: | Mercaptopurine |
| | Thioguanine |
| DNA Antimetabolites: | 3-HP |
| | 2'-deoxy-5-fluorouridine |
| | 5-HP |
| | alpha-TGDR |
| | aphidicolin glycinate |
| | ara-C |
| | 5-aza-2'-deoxycytidine |
| | beta-TGDR |
| | cyclocytidine |
| | guanazole |
| | inosine glycodialdehyde |
| | macebecin II |
| | Pyrazoloimidazole |

TABLE 2-continued

| Hormonal therapies: Receptor antagonists: | |
|---|---|
| Anti-estrogen: | Tamoxifen |
| | Raloxifene |
| | Megestrol |
| LHRH agonists: | Goserelin |
| | Leuprolide acetate |
| Anti-androgens: | Flutamide |
| | Bicalutamide |
| Retinoids/Deltoids | |
| | Cis-retinoic acid |
| Vitamin A derivative: | All-trans retinoic acid (ATRA-IV) |
| Vitamin D3 analogs: | EB 1089 |
| | CB 1093 |
| | KH 1060 |
| Photodynamic therapies: | Vertoporfin (BPD-MA) |
| | Phthalocyanine |
| | Photosensitizer Pc4 |
| | Demethoxy-hypocrellin A |
| | (2BA-2-DMHA) |
| Cytokines: | Interferon-α |
| | Interferon-β |
| | Interferon-γ |
| | Tumor necrosis factor |
| Angiogenesis Inhibitors: | Angiostatin (plasminogen fragment) |
| | antiangiogenic antithrombin III |
| | Angiozyme |
| | ABT-627 |
| | Bay 12-9566 |
| | Benefin |
| | Bevacizumab |
| | BMS-275291 |
| | cartilage-derived inhibitor (CDI) |
| | CAI |
| | CD59 complement fragment |
| | CEP-7055 |
| | Col 3 |
| | Combretastatin A-4 |
| | Endostatin (collagen XVIII fragment) |
| | Fibronectin fragment |
| | Gro-beta |
| | Halofuginone |
| | Heparinases |
| | Heparin hexasaccharide fragment |
| | HMV833 |
| | Human chorionic |
| | gonadotropin (hCG) |
| | IM-862 |
| | Interferon alpha/beta/gamma |
| | Interferon inducible protein (IP-10) |
| | Interleukin-12 |
| | Kringle 5 (plasminogen fragment) |
| | Marimastat |
| | Metalloproteinase inhibitors (TIMPs) |
| | 2-Methoxyestradiol |
| | MMI 270 (CGS 27023A) |
| | MoAb IMC-1C11 |
| | Neovastat |
| | NM-3 |
| | Panzem |
| | PI-88 |
| | Placental ribonuclease inhibitor |
| | Plasminogen activator inhibitor |
| | Platelet factor-4 (PF4) |
| | Prinomastat |
| | Prolactin 16 kD fragment |
| | Proliferin-related protein (PRP) |
| | PTK 787/ZK 222594 |
| | Retinoids |
| | Solimastat |
| | Squalamine |
| | SS 3304 |
| | SU 5416 |
| | SU6668 |
| | SU11248 |
| | Tetrahydrocortisol-S |
| | Tetrathiomolybdate |

TABLE 2-continued

| | |
|---|---|
| | Thalidomide |
| | Thrombospondin-1 (TSP-1) |
| | TNP-470 |
| | Transforming growth factor-beta (TGF-β) |
| | Vasculostatin |
| | Vasostatin (calreticulin fragment) |
| | ZD6126 |
| | ZD 6474 |
| | farnesyl transferase inhibitors (FTI) |
| | Bisphosphonates |
| Antimitotic agents: | Allocolchicine |
| | Halichondrin B |
| | Colchicine |
| | colchicine derivative |
| | dolstatin 10 |
| | Maytansine |
| | Rhizoxin |
| | Thiocolchicine |
| | trityl cysteine |
| Others: | |
| Isoprenylation inhibitors: | |
| Dopaminergic neurotoxins: | 1-methyl-4-phenylpyridinium ion |
| Cell cycle inhibitors: | Staurosporine |
| Actinomycins: | Actinomycin D |
| | Dactinomycin |
| Bleomycins: | Bleomycin A2 |
| | Bleomycin B2 |
| | Peplomycin |
| Anthracyclines: | Daunorubicin |
| | Doxorubicin (adriamycin) |
| | Idarubicin |
| | Epirubicin |
| | Pirarubicin |
| | Zorubicin |
| | Mitoxantrone |
| MDR inhibitors: | Verapamil |
| $Ca^{2+}$ ATPase inhibitors: | Thapsigargin |

Other anti-cancer agents that may be used in the present invention include, but are not limited to, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Further anti-cancer drugs that can be used in the present invention include, but are not limited to: 20-epi-1,25-dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum complexes; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti-cancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum complexes; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone BI; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

It is a further aspect of the invention the Compounds of the Invention can be administered in conjunction with chemical agents that are understood to mimic the effects of radiotherapy and/or that function by direct contact with DNA. Preferred agents for use in combination with the Compounds of the Invention for treating cancer include, but are not limited to cis-diamminedichloro platinum (II) (cisplatin), doxorubicin, 5-fluorouracil, taxol, and topoisomerase inhibitors such as etoposide, teniposide, irinotecan and topotecan.

Additionally, the invention provides methods of treatment of cancer using the Compounds of the Invention as an alternative to chemotherapy alone or radiotherapy alone where the chemotherapy or the radiotherapy has proven or can prove too toxic, e.g., results in unacceptable or unbearable side effects, for the subject being treated. The subject being treated can, optionally, be treated with another anticancer treatment modality such as chemotherapy, surgery, or immunotherapy, depending on which treatment is found to be acceptable or bearable.

The Compounds of the Invention can also be used in an in vitro or ex vivo fashion, such as for the treatment of certain cancers, including, but not limited to leukemias and lymphomas, such treatment involving autologous stem cell transplants. This can involve a multi-step process in which the subject's autologous hematopoietic stem cells are harvested and purged of all cancer cells, the subject is then administered an amount of a Compound of the Invention effective to eradicate the subject's remaining bone-marrow cell population, then the stem cell graft is infused back into the subject. Supportive care is then provided while bone marrow function is restored and the subject recovers.

5.8.1.4 Other Therapeutic Agents

The present methods for treating cancer can further comprise the administration of a Compound of the Invention and an additional therapeutic agent or pharmaceutically acceptable salts, solvates or hydrates thereof. In one embodiment, a composition comprising a Compound of the Invention is administered concurrently with the administration of one or more additional therapeutic agent(s), which may be part of the same composition or in a different composition from that comprising the Compound of the Invention. In another embodiment, a Compound of the Invention is administered prior to or subsequent to administration of another therapeutic agent(s).

In the present methods for treating cancer the other therapeutic agent may be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinols, thiethylperazine, thioproperazine and tropisetron.

In a preferred embodiment, the anti-emetic agent is granisetron or ondansetron.

In another embodiment, the other therapeutic agent may be an hematopoietic colony stimulating factor. Suitable hematopoietic colony stimulating factors include, but are not limited to, filgrastim, sargramostim, molgramostim and epoietin alfa.

In still another embodiment, the other therapeutic agent may be an opioid or non-opioid analgesic agent. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

In still another embodiment, the other therapeutic agent may be an anxiolytic agent. Suitable anxiolytic agents include, but are not limited to, buspirone, and benzodiazepines such as diazepam, lorazepam, oxazapam, chlorazepate, clonazepam, chlordiazepoxide and alprazolam.

5.8.2 Treatment of Neurological Diseases

Neurological diseases can be treated or prevented by administration of amounts of the Compounds of the invention that are effective to treat the neurological disease or by administration of a pharmaceutical composition comprising amounts of the Compounds of the invention that are effective to treat the neurological disease. In one embodiment, the neurological diseases that can be treated or prevented by administering a Compound of the Invention include, but are not limited to, Huntington's disease, lupus, schizophrenia, multiple sclerosis, muscular dystrophy, drug-induced movement disorders, Creutzfeldt-Jakob disease, amyotrophic lateral sclerosis, Pick's disease, Alzheimer's disease, Lewy body dementia, cortico basal degeneration, dystonia, myoclonus, Tourette's Syndrome, tremor, chorea, restless leg syndrome, Parkinson's disease, and Parkinsonian Syndromes, such as progressive supranuclear palsy, multiple system atrophy, Wilson's disease and mult-infarct state. In a preferred embodiment, the neurological disease treated is Huntingon's disease, lupus, or schizophrenia.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited throughout this specification, the entire disclosures of each of which have been incorporated herein by reference in their entireties for all purposes.

6. EXAMPLES

6.1 Example 1

Preparation of 4-[3-(4-Dimethylamino-benzyl)-ureido]-N-hydroxy-butyramide (2)

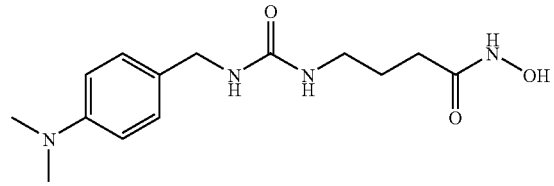

4-[3-(4-Dimethylamino-benzyl)-ureido]-butyric acid benzyl ester

To a vigorous stirred suspension of 4-amino-butyric acid benzyl ester toluene-4-sulfonic acid (0.730 g, 2.00 mmol) and triphosgene (0.200 g, 0.667 mmol) in dichloromethane (40 mL) at −78° C. under nitrogen atmosphere, was added triethylamine (1.0 mL, 7.188 mmol, in 10 mL dichloromethane) dropwise via an additional funnel over a period of 2 hours. The cooling bath was removed and the resulting reaction was allowed to stir at room temperature for 1 hour, after which time 4-dimethylaminobenzylamine dihydrochloride (0.446 g, 2.00 mmol) was added to the reaction mixture, followed by triethylamine (0.67 mL, 4.8 mmol). The resulting reaction was allowed to stir for about 18 h, then the reaction mixture was diluted with brine (20 mL), transferred to a separatory funnel and the aqueous layer was extracted with dichloromethane. The organic layer was dried over sodium sulfate and concentrated in vacuo to provide a crude residue which was purified by flash column chromatography (silica gel 60, $CH_2Cl_2$/EtOAc=4:1 to 2:1) to afford 4-[3-(4-Dimethylamino-benzyl)-ureido]-butyric acid benzyl ester (0.686 g, 93% yield). $^1$H NMR (300 MHz, $CDCl_3$) δ (ppm) 7.31 (m, 5H), 7.09 (d, J=9.0 Hz, 2H), 6.63 (d, J=9.0 Hz, 2H), 5.20 (t, J=5.4 Hz, 1H), 5.09 (t, J=5.4 Hz, 1H), 5.05 (s, 2H), 4.14 (d, J=5.7 Hz, 2H), 3.09 (dt, J=6.6, 6.3 Hz, 2H), 2.86 (s, 6H), 2.32 (t, J=7.5 Hz, 2H), 1.73 (m, 2H). $^{13}$C NMR (75 MHz, $CDCl_3$) δ (ppm) 173.3, 158.5, 149.8, 135.8, 128.5, 128.15, 128.09, 127.0, 112.6, 66.2, 43.9, 40.7, 39.5, 31.5, 25.4.

N-Benzyloxy-4-[3-(4-dimethylamino-benzyl)-ureido]-butyramide

To a solution of 4-[3-(4-dimethylamino-benzyl)-ureido]-butyric acid benzyl ester (626 mg, 1.696 mmol) in methanol (20 mL) was added 10% palladium on carbon (40 mg), and the resulting reaction was allowed to stir under a hydrogen atmosphere for 18 hr, after which time the reaction mixture was filtered and concentrated in vacuo to provide a crude residue.

To a suspension of the crude residue in dichloromethane (40 mL) was added EDCI (650 mg, 3.391 mmol) at 0° C., followed by the benzyloxyamine hydrochloride (541 mg, 3.389 mmol) and triethylamine (0.475 mL, 3.414 mmol). The cooling bath was removed and the resulting reaction was allowed to stir at room temperature for 18 h. The reaction mixture transferred to a separatory funnel, washed with brine (20 mL), and the aqueous layer was back extracted with dichloromethane. The combined organic extracts were dried over sodium sulfate and concentrated in vacuo to provide a crude residue which was purified using flash column chromatography (silica gel 60, CH$_2$Cl$_2$/MeOH=50:1 to 20:1) to provide N-Benzyloxy-4-[3-(4-dimethylamino-benzyl)-ureido]-butyramide (330 mg, 50% yield). $^1$H NMR (300 MHz, CDCl$_3$) δ (ppm) 9.98 (br s, 1H), 7.35 (m, 5H), 7.11 (d, J=8.7 Hz, 2H), 6.65 (d, J=8.7 Hz, 2H), 5.05 (br s, 2H), 4.86 (s, 2H), 4.16 (d, J=5.4 Hz, 2H), 3.09 (dt, J=6.6, 6.0 Hz, 2H), 2.89 (s, 6H), 2.02 (t, J=6.6 Hz, 2H), 1.68 (m, 2H). $^{13}$C NMR (75 MHz, CDCl$_3$) δ (ppm) 171.1, 159.0, 150.0, 129.1, 128.6, 128.5, 126.9, 112.8, 78.0, 44.1, 40.7, 38.9, 30.3, 26.8.

4-[3-(4-Dimethylamino-benzyl)-ureido]-N-hydroxy-butyramide (2)

To a solution of the N-benzyloxy-4-[3-(4-dimethylamino-benzyl)-ureido]-butyramide (287 mg, 0.747 mmol) in methanol (15 mL) was added 10% palladium on carbon (30 mg) and the resulting reaction was allowed to stir under a hydrogen atmosphere for 18 hr, after which time the reaction mixture was filtered and concentrated in vacuo to provide provide compound 2, which was used without further purification. (203 mg, 92% yield). $^1$H NMR (300 MHz, DMSO-d$_6$) δ (ppm) 10.38 (s, 1H), 8.69 (s, 1H), 7.06 (d, J=9.0 Hz, 2H), 6.67(d, J=9.0 Hz, 2H), 6.10 (t, J=5.4 Hz, 1H), 5.87 (t, J=5.4 Hz, 1H), 4.06 (d, J=5.7 Hz, 2H), 2.97 (dt, J=6.6, 6.3 Hz, 2H), 2.85 (s, 6H), 1.94 (t, J=7.2 Hz, 2H), 1.57 (m, 2H). $^{13}$C NMR (75 MHz, DMSO-d$_6$) δ (ppm) 168.8, 157.9, 149.4, 128.2, 127.9, 112.3, 42.4, 40.2, 38.8, 29.8, 26.3.

6.2 Example 2

Preparation of
5-[3-(4-dimethylamino-benzyl)-ureido]-pentanoic acid hydroxyamide (3)

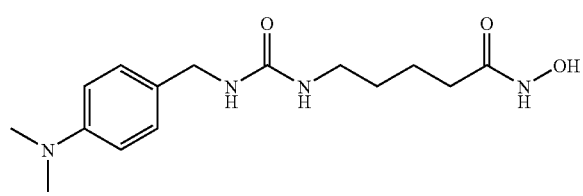

Compound 3 was prepared using the methodology described for the preparation of compound 2, by substituting 4-amino-butyric acid benzyl ester toluene-4-sulfonic acid with 5-amino-pentanoic acid benzyl ester toluene-4-sulfonic acid. $^1$H NMR (300 MHz, DMSO-d$_6$) δ (ppm) 10.35 (br s, 1H), 8.68 (br s, 1H), 7.06 (d, J=8.7 Hz, 2H), 6.67(d, J=8.7 Hz, 2H), 6.07 (t, J=5.4 Hz, 1H), 5.84 (t, J=5.4 Hz, 1H), 4.05 (d, J=6.0 Hz, 2H), 2.97 (dt, J=6.6, 6.3 Hz, 2H), 2.84 (s, 6H), 1.94 (t, J=7.2 Hz, 2H), 1.47 (m, 2H), 1.32 (m, 2H). $^{13}$C NMR (75 MHz, DMSO-d$_6$) δ (ppm) 168.7, 157.7, 149.2, 128.0, 127.7, 112.1, 42.2, 40.0, 38.6, 31.7, 29.4, 22.3.

6.3 Example 3

Preparation of
6-[3-(4-dimethylamino-benzyl)-ureido]-hexanoic acid hydroxyamide (4)

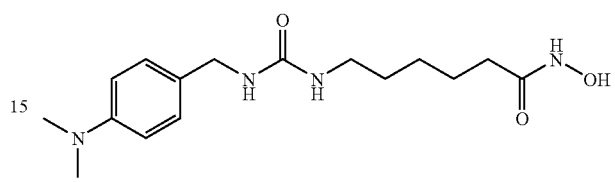

Compound 4 was prepared using the methodology described for the preparation of compound 2, by substituting 4-amino-butyric acid benzyl ester toluene-4-sulfonic acid with 6-amino-hexanoic acid benzyl ester toluene-4-sulfonic acid. $^1$H NMR (300 MHz, DMSO-d$_6$) δ (ppm) 10.34 (br, s, 1H), 8.67 (br s, 1H), 7.06 (d, J=8.7 Hz, 2H), 6.67 (d, J=8.7 Hz, 2H), 6.05 (t, J=5.7 Hz, 1H), 5.80 (t, J=5.7 Hz, 1H), 4.05 (d, J=6.3 Hz, 2H), 2.97 (dt, J=6.6, 6.3 Hz, 2H), 2.85 (s, 6H), 1.93 (t, J=7.5 Hz, 2H), 1.48 (m, 2H), 1.34 (m, 2H), 1.22 (m, 2H). $^{13}$C NMR (75 MHz, DMSO-d$_6$) δ (ppm) 168.7, 157.7, 149.2, 128.0, 127.7, 112.1, 42.2, 40.0, 38.9, 31.9, 29.5, 25.7, 24.6.

6.4 Example 4

Preparation of
7-[3-(4-dimethylamino-benzyl)-ureido]-heptanoic acid hydroyxamide (5)

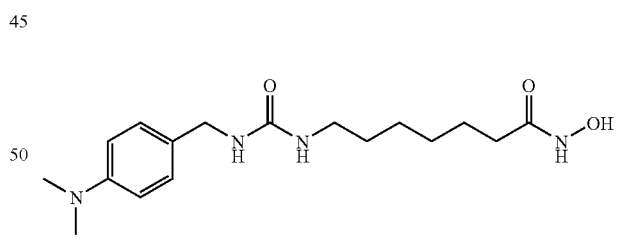

Compound 5 was prepared using the methodology described for the preparation of compound 2, by substituting 4-amino-butyric acid benzyl ester toluene-4-sulfonic acid with 7-amino-heptanoic acid benzyl ester toluene-4-sulfonic acid. $^1$H NMR (300 MHz, DMSO-d$_6$) δ (ppm) 10.33 (br, s, 1H), 8.66 (br s, 1H), 7.05 (d, J=8.7 Hz, 2H), 6.67 (d, J=8.7 Hz, 2H), 6.04 (t, J=5.7 Hz, 1H), 5.79 (t, J=5.7 Hz, 1H), 4.05 (d, J=6.0 Hz, 2H), 2.97 (dt, J=6.6, 6.6 Hz, 2H), 2.84 (s, 6H), 1.93 (t, J=7.5 Hz, 2H), 1.47 (m, 2H), 1.34 (m, 2H), 1.22 (m, 4H)

6.5 Example 5

Preparation of 8-[3-(4-dimethylamino-benzyl)-ureido]-octanoic acid hydroxyamide (6)

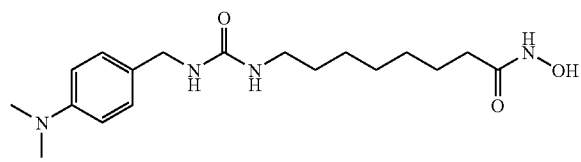

Compound 6 was prepared using the methodology described for the preparation of compound 2, by substituting 4-amino-butyric acid benzyl ester toluene-4-sulfonic acid with 8-amino-octanoic acid benzyl ester toluene-4-sulfonic acid. $^1$H NMR (300 MHz, DMSO-$d_6$) δ (ppm) 10.33 (br, s, 1H), 8.66 (br s, 1H), 7.05 (d, J=8.4 Hz, 2H), 6.67 (d, J=8.4 Hz, 2H), 6.05 (t, J=5.7 Hz, 1H), 5.81 (t, J=5.7 Hz, 1H), 4.05 (d, J=6.0 Hz, 2H), 2.97 (dt, J=6.6, 6.0 Hz, 2H), 2.85 (s, 6H), 1.93 (t, J=7.5 Hz, 2H), 1.47 (m, 2H), 1.34 (m, 2H), 1.24 (m, 6H).

6.6 Example 6

Preparation of 7-[3-(4-dimethylamino-phenyl)-ureido]-heptanoic acid hydroxyamide (7)

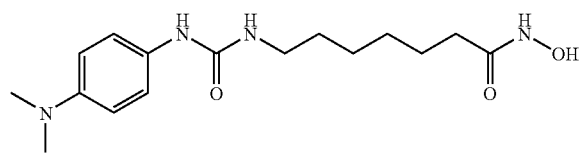

Compound 7 was prepared using the methodology described for the preparation of compound 2, by substituting 4-amino-butyric acid benzyl ester toluene-4-sulfonic acid with 7-amino-heptanoic acid benzyl ester toluene-4-sulfonic acid and 4-dimethylaminobenzylamine dihydrochloride with N,N-dimethyl-benzene-1,4-diamine dihydrochloride. $^1$H NMR (300 MHz, DMSO-$d_6$) δ (ppm) 10.34 (br, s, 1H), 8.64 (br s, 1H), 7.98 (br s, 1H), 7.17 (d, J=9.0 Hz, 2H), 6.65 (d, J=9.0 Hz, 2H), 5.91 (t, J=5.7 Hz, 1H), 3.03 (dt, J=6.6, 6.0 Hz, 2H), 2.79 (s, 6H), 1.94 (t, J=7.5 Hz, 2H), 1.48 (m, 2H), 1.39 (m, 2H), 1.25 (m, 4H).

6.7 Example 7

Preparation of 6-(3-adamantan-1-yl-ureido)-hexanoic acid hydroxyamide (8)

6-(3-Adamantan-1-yl-ureido)-hexanoic acid benzyl ester

To a vigorously stirred suspension of 6-amino-hexanoic acid benzyl ester toluene-4-sulfonic acid (0.786 g, 2.00 mmol) and triphosgene (0.200 g, 0.667 mmol) in dichloromethane (30 mL) at −78° C. under inert atmosphere, was added triethylamine (1.0 mL, 7.188 mmol, in 10 mL dichloromethane) dropwise via additional funnel over a period of 2 hours. The cooling bath was removed and the resulting reaction was allowed to stir at room temperature for 1 hour, after which time, 4-Dimethylaminobenzylamine dihydrochloride (0.303 g, 2.00 mmol) was added to the reaction mixture. After stirring overnight, the mixture was washed with brine (20 mL) and the aqueous layer was extracted with dichloromethane. The combined organic layers were dried over sodium sulfate and the solvent was evaporated. The residue was purified using flash column chromatography (silica gel 60, $CH_2Cl_2$/EtOAc 6:1 to 4:1) to afford 6-(3-Adamantan-1-yl-ureido)-hexanoic acid benzyl ester 0.481 g (61% yield). $^1$H NMR (300 MHz, $CDCl_3$) δ (ppm) 7.34 (m, 5H), 5.11 (s, 2H), 4.61 (t, J=5.7 Hz, 1H), 4.43 (s, 1H), 3.08 (dt, J=6.9, 5.7 Hz, 2H), 2.35 (t, J=7.5 Hz, 2H), 2.04 (m, 3H), 1.94 (m, 6H), 1.65 (m, 8H) 1.46 (m, 2H) 1.31 (m, 2H). $^{13}$C NMR (75 MHz, $CDCl_3$) δ (ppm) 173.5, 157.4, 135.9, 128.5, 128.2, 128.1, 66.1, 50.6, 42.5, 39.8, 36.4, 34.1, 29.9, 29.5, 26.4, 24.5.

6-(3-Adamantan-1-yl-ureido)-hexanoic acid hydroxyamide (8)

To a solution of 6-(3-adamantan-1-yl-ureido)-hexanoic acid benzyl ester (440 mg, 1.696 mmol) in methanol (20 mL) was added 10% palladium on carbon (40 mg), and the resulting reaction was allowed to stir under a hydrogen atmosphere for 18 hr, after which time the reaction mixture was filtered and concentrated in vacuo to provide a crude residue (343 mg).

To a suspension of the crude residue in dichloromethane (40 mL) was added EDCI (427 mg, 2.23 mmol) at 0° C., followed by the addition of benzyloxyamine hydrochloride (267 mg, 1.67 mmol) and triethylamine (0.23 mL, 1.67 mmol). The cooling bath was removed and the mixture was allowed to stir at room temperature overnight. The resulting reaction was allowed to stir for about 18 h, then the reaction mixture was diluted with brine (20 mL), transferred to a separatory funnel and the aqueous layer was extracted with dichloromethane. The organic layer was dried over sodium sulfate and concentrated in vacuo to provide a crude residue which was purified by flash column chromatography to provide amide (262 mg).

To a solution of the amide in methanol (15 mL) was added 10% palladium on carbon (30 mg). After it was treated with hydrogen under atmosphere pressure overnight, the reaction mixture was filtered and concentrated to provide compound 8 (184 mg, 51% yield from 6-(3-adamantan-1-yl-ureido)-hexanoic acid benzyl ester). $^1$H NMR (300 MHz, $CD_3OD$) δ (ppm) 3.04 (t, J=7.2 Hz, 2H), 2.09 (t, J=7.5 Hz, 2H), 2.03 (m, 3H), 1.96 (m, 6H), 1.70 (m, 6H), 1.62 (m, 2H), 1.45 (m, 2H), 1.34 (m, 2H). $^{13}$C NMR (75 MHz, $CD_3OD$) δ (ppm) 173.0, 160.5, 51.5, 43.6, 40.5, 37.7, 33.8, 31.19, 31.14, 27.5, 26.6.

6.8 Example 8

Preparation of 2-mercapto-N-[5-(3-phenyl-ureido)-pentyl]-acetamide (9)

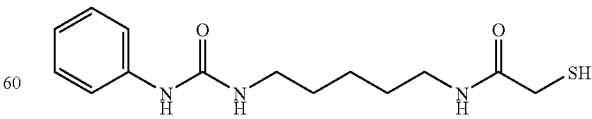

Tritylsulfanyl-acetic acid methyl ester

To a mixture of methyl mercaptoacetate (5.30 g, 50 mmol) and triphenylmethanol (13.0 g, 50 mmol) in chloroform (20 mL) was added trifloroacetic acid (5 mL) in 5 min. After stirring at room temperature for 1 h, the volatiles were removed in vacuo. The crude product was purified by recrystallization (dichloromethane/Hexane=½) to provide Tritylsulfanyl-acetic acid methyl ester (15.9 g, 91%). ¹H NMR (300 MHz, CDCl₃) δ 7.44-7.38 (m, 6H), 7.34-7.18 (m, 9H), 3.58 (s, 3H), 2.98 (s, 2H).

7-Amino-1-tritylsulfanyl-heptan-2-one 1,5-Diaminopentane (0.75 g, 7.21 mmol) was stirred while tritylsulfanyl-acetic acid methyl ester (2.53 g, 7.27 mmol) was added slowly. The mixture was heated at 100° C. for 2 h while methyl alcohol escaped. The product was isolated by column chromatography (dichloromethane/MeOH/Et₃N=10/1/0.1) to provide 7-Amino-1-tritylsulfanyl-heptan-2-one (1.63 g, 54%). ¹H NMR (300 MHz, CD₃OD) δ 7.42-7.36 (m, 6H), 7.31-7.18 (m, 9H), 3.00 (t, J=6.9 Hz, 2H), 2.60 (t, J=6.9 Hz, 2H), 1.42 (m, 4H), 1.27 (m, 2H). ¹³C NMR (75 MHz, CD₃OD) δ 171.1, 145.8, 130.9, 129.2, 128.2, 68.4, 42.5, 40.8, 37.4, 33.4, 30.1, 25.3.

2-Mercapto-N-[5-(3-phenyl-ureido)-pentyl]-acetamide (9)

To a solution of 7-amino-1-tritylsulfanyl-heptan-2-one (0.36 g, 0.86 mmol) in dichloromethane (10 mL) was added phenylisocyanate (0.10 ml, 0.92 mmol). The mixture was stirred at room temperature for 2 h. Solvent was then removed in vacuo and the crude product was purified by column chromatography (dichloromethane/MeOH=100/1 to 40/1) to provide 1-(6-Oxo-7-tritylsulfanyl-heptyl)-3-phenyl-urea (0.43 g, 93%).

To a solution of 1-(6-oxo-7-tritylsulfanyl-heptyl)-3-phenyl-urea (0.420 g, 0.78 mmol) in dichloromethane was added trifluoroacetic acid (0.50 mL, 6.49 mmol), followed by the addition of triethylsilane (0.18 mL, 1.13 mmol). After stirring at room temperature for 2 h, the volatiles were removed in vacuo and the crude product was purified by column chromatography (dichloromethane/MeOH=60/1 to 20/1) to provide compound 9 (0.216 g, 94%). ¹H NMR (300 MHz, DMSO-d₆) δ (ppm) 8.39 (br, s, 1H), 7.99 (br t, J=5.1 Hz, 1H), 7.38 (d, J=7.5 Hz, 2H), 7.21 (d, J=7.5 Hz, 2H), 6.87 (t, J=7.5 Hz, 1H), 6.10 (br s, 1H), 3.08 (d, J=7.8 Hz, 2H), 3.05 (t, J=6.9 Hz, 2H), 2.71 (t, J=7.8 Hz, 1H), 1.43 (m, 4H), 1.28 (m, 2H). ¹³C NMR (75 MHz, DMSO-d₆) δ (ppm) 169.4, 155.2, 140.6, 128.6, 120.9, 117.6, 38.9, 38.8, 29.5, 28.7, 27.2, 23.8.

6.9 Example 9

Preparation of 2-Mercapto-N-[6-(3-phenyl-ureido)-hexyl]-acetamide (10)

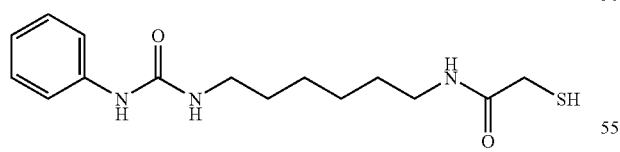

Compound 10 was prepared using the methodology described for the preparation of compound 9, by substituting 1,5-diaminopentane with 1,6-diaminohexane. ¹H NMR (300 MHz, DMSO-d₆) δ (ppm) 8.37 (br s, 1H), 7.97 (br t, J=5.1 Hz, 1H), 7.37 (d, J=7.5 Hz, 2H), 7.20 (t, J=7.5 Hz, 2H), 6.87 (t, J=7.5 Hz, 1H), 6.10 (br t, J=5.4 Hz, 1H), 3.07 (d, J=7.8 Hz, 2H), 3.04 (t, J=6.9 Hz, 2H), 2.71 (t, J=7.8 Hz, 1H), 1.41 (m, 4H), 1.28 (m, 4H). ¹³C NMR (75 MHz, DMSO-d₆) δ (ppm) 169.4, 155.2, 140.6, 128.6, 120.9, 117.5, 38.96, 38.79, 29.7, 29.0, 27.1, 26.1 (2C).

6.10 Example 10

Preparation of N-[5-(3-benzyl-ureido)-pentyl]-2-mercapto-acetamide (11)

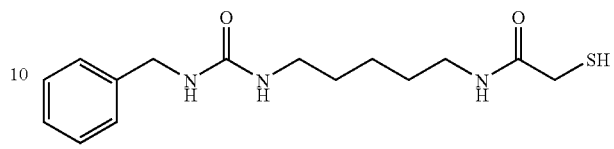

Compound 11 was prepared using the methodology described for the preparation of Compound 9, by substituting phenylisocyanate with benzylisocyanate. ¹H NMR (300 MHz, DMSO-d₆) δ (ppm) 7.98 (br s, 1H), 7.35-7.18 (m, 5H), 6.27 (br s, 1H), 5.91 (br s, 1H), 4.19 (s, 2H), 3.07 (d, J=8.1 Hz, 2H), 3.02 (m, 4H), 2.71 (t, J=8.1 Hz, 1H), 1.37 (m, 4H), 1.26 (m, 2H). ¹³C NMR (75 MHz, DMSO-d₆) δ (ppm) 169.4, 158.1, 141.0, 128.2, 127.0, 126.5, 42.9, 39.2, 38.8, 29.7, 28.7, 27.1, 23.7.

6.11 Example 11

Preparation of N-{6-[3-(4-dimethylamino-benzyl)-ureido]-hexyl}-2-mercapto-acetamide (12)

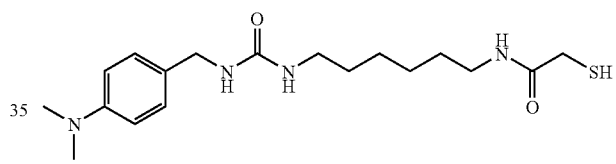

Compound 12 was prepared using the methodology described for the preparation of compound 9, by substituting 1,5-diaminopentane with 1,6-diaminohexane and phenylisocyanate with (4-isocyanato-phenyl)-dimethyl-amine. ¹H NMR (300 MHz, DMSO-d₆) δ (ppm) 7.98 (br s, 1H), 7.05 (d, J=8.7 Hz, 2H), 6.60 (d, J=8.7 Hz, 2H), 6.04 (br t, J=5.7 Hz, 1H), 5.80 (br t, J=5.7 Hz, 1H), 4.05 (d, J=5.7 Hz, 2H), 3.06 (d, J=8.1 Hz, 2H), 3.04 (dt, J=6.9, 6.0 Hz, 2H), 2.98 (dt, J=6.6, 6.0 Hz, 2H), 2.84 (s, 6H), 2.71 (t, J=8.1 Hz, 1H), 1.36 (m, 4H), 1.24 (m, 4H). ¹³C NMR (75 MHz, DMSO-d₆) δ (ppm) 169.2, 157.9, 149.3, 127.9, 126.9, 112.3, 42.4, 40.3, 39.1, 38.7, 30.0, 29.0, 27.1, 26.12, 26.08.

6.12 Example 12

Preparation of 2-mercapto-N-[6-(3-phenyl-ureido)-hexyl]-acetamide (13)

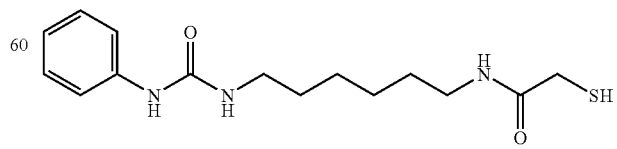

Compound 13 was prepared using the methodology described for the preparation of compound 9, by substituting 1,5-diaminopentane with 1,6-diaminohexane. $^1$H NMR (300 MHz, DMSO-$d_6$) δ (ppm) 8.37 (br s, 1H), 7.97 (br t, J=5.1 Hz, 1H), 7.37 (d, J=7.5 Hz, 2H), 7.20 (t, J=7.5 Hz, 2H), 6.87 (t, J=7.5 Hz, 1H), 6.10 (br t, J=5.4 Hz, 1H), 3.07 (d, J=7.8 Hz, 2H), 3.04 (t, J=6.9 Hz, 2H), 2.71 (t, J=7.8 Hz, 1H), 1.41 (m, 4H), 1.28 (m, 4H). $^{13}$C NMR (75 MHz, DMSO-$d_6$) δ (ppm) 169.4, 155.2, 140.6, 128.6, 120.9, 117.5, 38.96, 38.79, 29.7, 29.0, 27.1, 26.1 (2C).

6.13 Example 13

Preparation of N-hydroxy-3-[3-(2-hydroxy-2-phenyl-ethyl)-ureido]-propionamide (14)

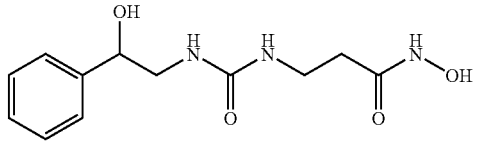

Compound 14 was prepared using the methodology described for the preparation of Compound 2, by substituting 4-amino-butyric acid benzyl ester toluene-4-sulfonic acid with 3-amino-propionic acid benzyl ester toluene-4-sulfonic acid and 4-dimethylaminobenzylamine dihydrochloride with 2-amino-1-phenyl-ethanol. $^1$H NMR (CD$_3$OD) δ 7.40-7.22 (m, 5H), 4.69 (dd, J=7.8, 4.2 Hz, 1H), 3.41-3.34 (m, 3H), 3.22 (dd, J=13.8, 7.8 Hz, 1H), 2.25 (t, J=6.9 Hz, 2H). $^{13}$C NMR (CD$_3$OD) δ 171.1, 161.3, 144.2, 129.5, 128.7, 127.3, 74.6, 48.9, 37.5, 34.7.

6.14 Example 14

Preparation of N-hydroxy-4-[3-(2-hydroxy-2-phenyl-ethyl)-ureido]-butyramide (15)

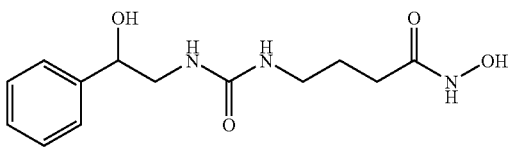

Compound 15 was prepared using the methodology described for the preparation of compound 2, by substituting 4-dimethylaminobenzylamine dihydrochloride with 2-amino-1-phenyl-ethanol. $^1$H NMR (CD$_3$OD) δ 7.42-7.24 (m, 5H), 4.73 (dd, J=7.8, 4.2 Hz, 1H), 3.43 (dd, J=13.8, 4.2 Hz, 1H), 3.26 (dd, J=13.8, 7.8 Hz, 1H), 3.14 (t, J=6.9 Hz, 2H), 2.12 (t, J=7.2 Hz, 2H), 1.76 (m, 2H). $^{13}$C NMR (CD$_3$OD) δ 172.7, 161.5, 144.2, 129.5, 128.7, 127.3, 74.6, 48.1, 39.4, 30.6, 27.0.

6.15 Example 15

Preparation of N-Hydroxy-4-(3-phenethyl-ureido)-butyramide (1)

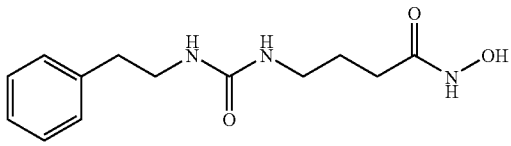

Compound 1 was prepared using the methodology described for the preparation of compound 2, by substituting 4-dimethylaminobenzylamine dihydrochloride with phenethylamine. $^1$H NMR (CD$_3$OD) δ 7.30-7.15 (m, 5H), 3.34 (t, J=6.9 Hz, 2H), 3.11 (t, J=7.2 Hz, 2H), 2.76 (t, J=7.2 Hz, 2H), 2.09 (t, J=7.5 Hz, 2H), 1.73 (m, 2H). $^{13}$C NMR (CD$_3$OD) δ 172.7, 161.3, 140.9, 130.0, 129.6, 127.4, 42.8, 40.4, 37.7, 31.3, 27.8.

6.16 Example 16

Preparation of octanedioic acid adamantan-1-ylamide hydroxyamide (17)

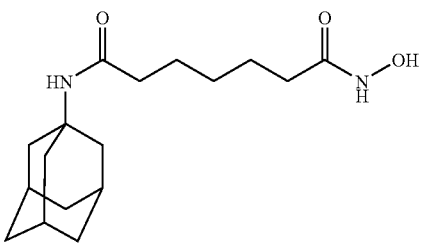

7-(Adamantan-1-yl-carbamoyl)-heptanoic acid methyl ester

To a solution of oxonane-2,9-dione (323 mg, 2.071 mmol) in THF (25 mL) was added 1-adamantanamine (312 mg, 2.066 mmol). The resulting reaction was allowed to stir at room temperature for 16 hours, then concentrated in vacuo to provide a crude residue which was diluted with methanol (20 mL) and treated with AG 50W X-2 acid resin (60 mg). The resulting reaction was heated at reflux with stirring for 5 hours, then the reaction mixture was cooled to room temperature, filtered and concentrated in vacuo. The resulting residue was purified using flash column chromatography (silica gel 60, CH$_2$Cl$_2$/EtOAc=5:1) to provide 7-(adamantan-1-yl-carbamoyl)-heptanoic acid methyl ester as a white solid (516 mg, 78% yield from 1-adamantanamine 5). $^1$H NMR (300 MHz, CDCl$_3$) δ 5.16 (br s, 1H), 3.66 (s, 3H), 2.30 (t, J=7.5 Hz, 2H), 2.07 (m, 5H), 1.99 (m, 6H), 1.67 (m, 6H), 1.67 (m, 6H), 1.61 (m, 4H), 1.32 (m, 4H). $^{13}$C NMR (75 MHz, CDCl$_3$) δ 174.2, 172.1, 51.7, 51.4, 41.6, 37.6, 36.3, 34.0, 29.4, 28.8, 28.7, 25.5, 24.7.

Octanedioic acid adamantan-1-ylamide hydroxyamide (17)

To a first solution of hydroxylamine hydrochloride (66 mg, 0.950 mmol) and phenolphthalein (0.5 mg) in methanol (3 mL), was added dropwise a second solution of sodium metal (33 mg, 1.435 mmol) in methanol (3 mL) via additional funnel until a pink endpoint was reached and precipitate appeared. To the reaction mixture was added a solution of 7-(adamantan-1-yl-carbamoyl)-heptanoic acid methyl ester (152 mg, 0.474 mmol) in methanol (4 mL) was added, followed by the remainder of the second solution of sodium metal in methanol. The resulting reaction was allowed to stir for 24 hours, then the reaction mixture was diluted with water (15 mL), followed by glacial acetic acid (0.2 mL) with stirring. The resulting precipitate was suction filtered and rinsed using water, then dried at room temperature under vacuum to provide a crude residue which was purified by recrystallization from dichloromethane/hexane to provide Compound 17 (104 mg, 68% yield). $^1$H NMR (300 MHz, CD$_3$OD) δ 7.31 (br s, 1H), 2.09 (t, J=7.5 Hz, 2H), 2.08-1.98 (m, 11H), 1.71 (m, 6H), 1.59 (m, 4H), 1.33 (m, 4H). $^{13}$C NMR (75 MHz, CD$_3$OD) δ 175.7, 173.1, 52.8, 42.5, 38.0, 37.7, 33.9, 31.1, 30.00, 29.96, 27.2, 26.8.

6.17 Example 17

Preparation of octanedioic acid hydroxyamide [2-(7-hydroxycarbamoyl-heptanoylamino)-phenyl]-amide (18)

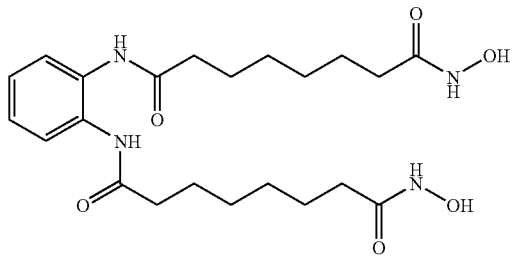

Compound 18 was prepared using the methodology described for the preparation of compound 17, by substituting 1-adamantanamine with benzene-1,2-diamine. $^1$H NMR (300 MHz, CD$_3$OD) δ 7.46 (m, 2H), 7.22 (m, 2H), 2.41 (t, J=7.5, 2H), 2.10 (t, J=7.5 Hz, 2H), 1.71 (m, 4H), 1.64 (m, 4H), 1.40 (m, 8H). $^{13}$C NMR (75 MHz, CD$_3$OD) δ 175.0, 173.0, 132.2, 127.2, 126.7, 37.6, 33.7, 29.98, 29.89, 26.77, 26.64.

6.18 Example 18

Preparation of N-[6-(3-phenyl-ureido)-hexyl]-2-{[6-(3-phenyl-ureido)-hexylcarbamoyl]-methyldisulfanyl}-acetamide (19)

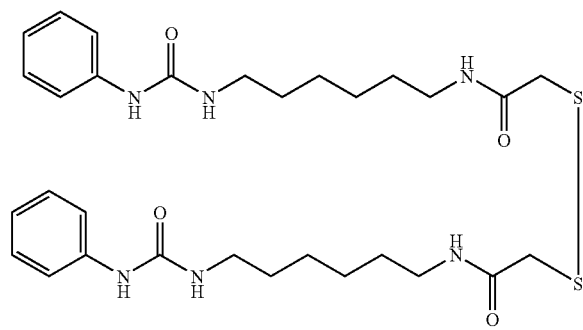

To a solution of 2-mercapto-N-[6-(3-phenyl-ureido)-hexyl]-acetamide (130 mg) in CH$_2$Cl$_2$ (10 mL) and MeOH (2 mL) was added Et$_3$N (0.1 mL). Oxygen was then bubbled through the resulting solution for 3 h with vigorous stirring. The reaction mixture was concentrated in vacuo and the resulting crude residue was purified using flash column chromatography (CH$_2$Cl$_2$/MeOH=60/2-60/4) to provide Compound 19 (122 mg, 94%). $^1$H NMR (300 MHz, DMSO-d$_6$) δ (ppm) 8.36 (br s, 2H), 8.07 (br t, J=5.4 Hz, 2H), 7.37 (d, J=7.5 Hz, 4H), 7.20 (t, J=7.5 Hz, 4H), 6.87 (t, J=7.5 Hz, 2H), 6.10 (br t, J=5.4 Hz, 2H), 3.46 (s, 4H), 3.07 (m, 8H), 1.41 (m, 8H), 1.28 (m, 8H). $^{13}$C NMR (75 MHz, DMSO-d$_6$) δ (ppm) 167.6, 155.2, 140.6, 128.6, 120.9, 117.5, 42.0, 38.97, 38.89, 29.7, 29.0, 26.13, 26.10.

6.19 Example 19

Preparation of N-{6-[3-(4-dimethylamino-benzyl)-ureido]-hexyl}-2-({6-[3-(4-dimethylamino-benzyl)-ureido]-hexylcarbamoyl}-methyldisulfanyl)-acetamide (20)

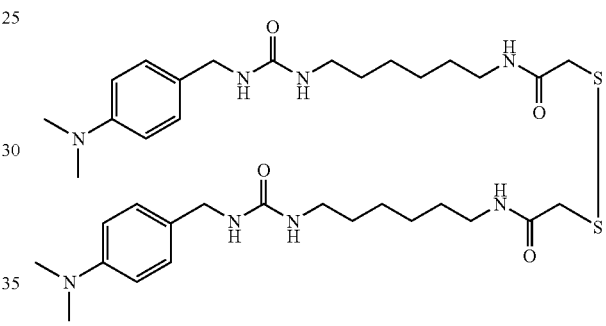

Compound 20 was prepared using the methodology described for the preparation of compound 19, by substituting 2-mercapto-N-[6-(3-phenyl-ureido)-hexyl]-acetamide with N-{6-[3-(4-dimethylamino-benzyl)-ureido]-hexyl}-2-mercapto-acetamide. $^1$H NMR (300 MHz, DMSO-d$_6$) δ (ppm) 8.07 (br t, J=5.4 Hz, 2H), 7.05 (d, J=8.4 Hz, 4H), 6.60 (d, J=8.4 Hz, 4H), 6.05 (br t, J=6.0 Hz, 2H), 5.81 (br t, J=5.7 Hz, 2H), 4.05 (d, J=5.7 Hz, 4H), 3.45 (s, 4H), 3.06 (dt, J=6.6, 6.0 Hz, 4H), 2.97 (dt, J=6.3, 6.0 Hz, 4H), 2.84 (s, 12H), 1.45-1.18 (m, 16H). $^{13}$C NMR (75 MHz, DMSO-d$_6$) δ (ppm) 167.4, 157.9, 149.3, 127.9, 126.9, 112.3, 42.4, 41.8, 40.3, 39.1, 38.7, 29.9, 28.9, 26.01, 25.95.

6.20 Example 20

Inhibition of HDAC Activity Assay

The HDAC activity inhibition assay was performed as follows, with data for selected compounds being listed in Table 3: Nuclear extracts from HeLa cells were prepared in 0.1 M KCl, 20 mM HEPES/NaOH at pH 7.9, 20% glycerol, 0.2 mM DTA, 0.5 mM DTT, and 0.5 mM PMSF (J. D. Dignam et al. Nuc. Acids Res 11:1475, 1983). Nuclear extract were mixed with Fluor de Lys substrate and the indicated concentrations of the Compounds of the Invention at 37° C. in HDAC assay buffer containing 25 mM Tris/Cl, pH 8.0, 137 mM NaCl, 2.7 mM KCl, and 1 mM MgCl$_2$. The resulting reactions were quenched after 15 min via the addition of Fluor de Lys Developer and fluorescence was measured at an exci tation wavelength of 360 nm and a detection of emitted light of 460 nm (TECAN ULTRA 384). For each test sample the corresponding assay reaction was performed in triplicate. Test samples include a Blank sample (no enzyme), a Control sample (no inhibitor), a negative control (MD83A), positive controls (TSA and SAHA), and selected Compounds of the Invention. For the selected Compounds of the Invention, samples at the following concentrations were prepared and tested: 1 µM, 5 µM, 10 µM, 100 µM and 1 mM. TSA and SAHA were used at concentrations of 0.5-5 µM. M83A was used at its $IC_{50}$ concentration (3 µM).

Results for selected compounds of the invention in the HDAC activity inhibition assay are presented in Table 3 (for 50% inhibition of HDAC activity) and in FIG. 1.

TABLE 3

HDAC Activity Inhibition Assay Data For Selected Compounds

| Compound | Compound No. | 50% HDAC activity inhibition | Cytotoxicity in SQ-20B cells ($IC_{50}$) |
|---|---|---|---|
| [structure] | TSA | 300 nM | 200 nM |
| [structure] | SAHA | 700 nM | 3 µM |
| [structure] | 2 | 800 nM | 50 µM |
| [structure] | 3 | 800 nM | 25 µM |
| [structure] | 5 | 1 µM | 50 µM |
| [structure] | 6 | 700 nM | 50 µM |
| [structure] | 7 | 700 nM | 10 µM |

TABLE 3-continued

HDAC Activity Inhibition Assay Data For Selected Compounds

| Compound | Compound No. | 50% HDAC activity inhibition | Cytotoxicity in SQ-20B cells (IC$_{50}$) |
|---|---|---|---|
| adamantyl-NH-C(O)-NH-(CH$_2$)$_4$-C(O)-NH-OH | 8 | 800 nM | 50 µM |
| Ph-NH-C(O)-NH-(CH$_2$)$_4$-NH-C(O)-CH$_2$-SH | 9 | 900 nM | NA |
| Ph-NH-C(O)-NH-(CH$_2$)$_5$-NH-C(O)-CH$_2$-SH | 10 | 900 nM | 50 µM |
| Bn-NH-C(O)-NH-(CH$_2$)$_5$-NH-C(O)-CH$_2$-SH | 11 | 1.6 µM | NA |
| Ph-C(O)-NH-(CH$_2$)$_5$-NH-C(O)-CH$_2$-SH | 21 | 1.6 µM | NA |
| 4-(Me$_2$N)-C$_6$H$_4$-C(O)-NH-(CH$_2$)$_5$-NH-C(O)-CH$_2$-SH | 22 | 800 nM | NA |
| 4-biphenyl-C(O)-NH-(CH$_2$)$_4$-NH-C(O)-CH$_2$-SH | 23 | 750 nM | NA |
| 4-(Me$_2$N)-C$_6$H$_4$-C(O)-NH-(CH$_2$)$_4$-NH-C(O)-CH$_2$-SH | 24 | 800 nM | NA |

TABLE 3-continued

HDAC Activity Inhibition Assay Data For Selected Compounds

| Compound | Compound No. | 50% HDAC activity inhibition | Cytotoxicity in SQ-20B cells (IC$_{50}$) |
|---|---|---|---|
| [structure: benzamide-NH-(CH$_2$)$_4$-NH-C(O)-CH$_2$-SH] | 25 | 1 µM | NA |

6.21 Example 21

Determination of Cytotoxicity in SQ-20B cells

To determine cytotoxicities of the Compounds of the Invention, human squamous carcinoma cells (SQ-20B), which exhibit a radiation resistant phenotype, were treated with the Compounds of the Invention at 0, 10 µM, 50 µM, 100 µM, 300 µM, 500 µM and 1 mM. For each concentration indicated, individual T25 flasks were seeded with the following number of SQ-20B cells: for no drug, 10 µM and 50 µM drug concentrations, separate T25 flasks were each seeded with 100 cells; for 100 µM and 300 µM drug concentrations, separate T25 flasks were each seeded with 200 cells each; and for 500 µM and 1 mM drug concentrations, separate T25 flasks were each seeded with 300 cells each. A Levy Hemacytometer (Hausser Scientific) was used to count the cells in stock suspension. Serial dilutions of stock suspension were performed to obtain the proper concentration for cell seeding. To conduct the cytotoxicity study the SQ20B cells were first seeded under the appropriate treatment specifications and allowed to settle for 24 hr in a tissue culture incubator set at 37° C. and 5% CO$_2$. Cells were treated with their corresponding drugs for 24 hr and then washed with three rinses of PBS (10 ml per rinse) and provided with new media. The cells were then further incubated for colony formation and the colonies were stained using a staining solution consisting of: 5 g Crystal Violet, 700 ml methanol and 300 ml dH$_2$O. The flasks were then destained with three rinses in cold water. After the third rinse the stained colonies were counted and the corresponding IC$_{50}$ for each drug was calculated.

6.22 Example 22

Determination of Radiation Sensitization

To test the ability of the Compounds of the Invention to sensitize cells to radiation, we used radiation resistant squamous carcinoma cell line, SQ-20B, for initial radiosensitization experiments. SQ-20B is extremely resistant to ionizing radiation (Do=2.4 Gy in the absence of radiation sensitizers). Briefly, logarithmically growing SQ-20B cells were treated with a drug compound at the IC$_{50}$ concentration (determined using the clonogenic survival assay illustrated in Example 21) for 24 h and then exposed to graded dose of gamma radiation. Clonogenic survivals were determined and fit to the single hit multi-target and the linear quadratic models.

The shape of radiation survival curves are determined by using either the single-hit multitarget model or the linear-quadratic model. The multitarget model is used to describe the radiation sensitivity of cells defined by the terminal slope of the radiation survival curve, which is referred to as Do. The steeper the slope, the smaller is the value of Do and the more radiation sensitive is the cellular response. Alternatively, a less steep slope results in a larger Do and a more resistant radiation response. The linear-quadratic model is also used to describe the radiation sensitivity defined by two components to cell killing by radiation: one is proportional to dose ($\alpha$D) and the other is proportional to the square of the dose ($\beta$D$^2$). Thus, the dose at which the linear and quadratic components are equal is the ratio $\alpha$/$\beta$.

Shown in Table 4 are the results of selected compounds of the invention in the radiation clonigenic survival assay.

TABLE 4

Radiation Clonigenic Survival Data for Selected Compounds

| Compound | Compound No. | Do in SQ-20B Cells (Gy) | α | β |
|---|---|---|---|---|
| [structure: TSA - trichostatin A] | TSA | 1.65 | 0.1260 | 0.03059 |
| [structure: SAHA] | SAHA | 1.88 | 0.01197 | 0.03152 |

TABLE 4-continued

Radiation Clonigenic Survival Data for Selected Compounds

| Compound | Compound No. | Do in SQ-20B Cells (Gy) | α | β |
|---|---|---|---|---|
| (structure) | 2 | 1.62 | 0.1681 | 0.03301 |
| (structure) | 3 | 1.72 | 0.2420 | 0.02486 |
| (structure) | 5 | 1.78 | 0.1978 | 0.02561 |
| (structure) | 6 | 1.94 | 0.2846 | 0.01761 |
| (structure) | 7 | 1.57 | 0.1391 | 0.03335 |
| (structure) | 8 | 1.78 | 0.2378 | 0.02282 |
| (structure) | 10 | 2.54 | 0.1135 | 0.01558 |

*For SQ-20B cells in the absence of radiation sensitizers, the Do is 2.4 Gy.

7. REFERENCES CITED

Each and every reference cited herein is hereby incorporated in its entirety for all purposes to the same extent as if each reference were individually incorporated by reference. Furthermore, while the invention has been described in detail with reference to preferred embodiments thereof, it will be apparent to one skilled in the art that various changes can be made, and equivalents employed, without departing from the scope of the invention.

What is claimed is:

1. A compound having the formula

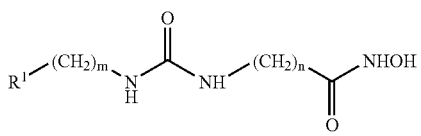

(I)

or a pharmaceutically acceptable salt thereof,
wherein
$R^1$ is aryl, which may be unsubstituted or substituted with one or more of the following groups: —$C_1$-$C_6$ alkyl, —O—($C_1$-$C_6$ alkyl), —OH, —CN, —COOR', —OC(O)R', NHR', N(R')$_2$, —NHC(O)R' or —C(O)NHR' groups wherein R' is —H or unsubstituted —$C_1$-$C_6$ alkyl,
m is an integer ranging from 1-10; and
n is an integer ranging from 1-10.

2. The compound of claim 1 wherein $R^1$ is phenyl.

3. The compound of claim 1 wherein n is an integer ranging from 1-5.

4. The compound of claim 1 wherein m is 2.

5. The compound of claim 1 wherein $R^1$ is phenyl, m is 2 and n is 3.

6. The compound of claim 1 wherein $R^1$ is -4-N(CH$_3$)$_2$-phenyl and m is 1.

7. The compound of claim 1 wherein $R^1$ is -4-N(CH$_3$)$_2$-phenyl, m is 1 and n is 4.

8. The compound of claim 1 wherein $R^1$ is -4-N(CH$_3$)$_2$-phenyl, m is 1 and n is 5.

9. A pharmaceutical composition comprising the compound or a pharmaceutically acceptable salt of the compound of claim 1 and a pharmaceutically acceptable carrier or vehicle.

10. The compound of claim 1 wherein $R^1$ is -4-N(CH$_3$)$_2$-phenyl, m is 1 and n is 6.

11. The compound of claim 1 wherein $R^1$ is -4-N(CH$_3$)$_2$-phenyl, m is 1 and n is 7.

* * * * *